US011123091B2

(12) United States Patent
Eaton et al.

(10) Patent No.: US 11,123,091 B2
(45) Date of Patent: Sep. 21, 2021

(54) DEVICE AND METHODS FOR TREATING PARANASAL SINUS CONDITIONS

(71) Applicant: Intersect ENT, Inc., Menlo Park, CA (US)

(72) Inventors: Donald J. Eaton, Los Altos, CA (US); Thomas R. Tice, Indian Springs, AL (US); David B. Downie, Cupertino, CA (US); Patrick A. Arensdorf, Palo Alto, CA (US); Rodney A. Brenneman, San Juan Capistrano, CA (US); Danielle L. Clay, Hoover, AL (US)

(73) Assignee: Intersect ENT, Inc., Menlo Park, CA (US)

( * ) Notice: Subject to any disclaimer, the term of this patent is extended or adjusted under 35 U.S.C. 154(b) by 26 days.

(21) Appl. No.: 15/415,465

(22) Filed: Jan. 25, 2017

(65) Prior Publication Data

US 2017/0128093 A1    May 11, 2017

Related U.S. Application Data

(63) Continuation of application No. 12/883,087, filed on Sep. 15, 2010, now Pat. No. 9,585,681, which is a
(Continued)

(51) Int. Cl.
*A61B 17/24* (2006.01)
*A61K 9/00* (2006.01)
(Continued)

(52) U.S. Cl.
CPC ............ *A61B 17/24* (2013.01); *A61K 9/0043* (2013.01); *A61K 9/70* (2013.01); *A61K 31/573* (2013.01);
(Continued)

(58) Field of Classification Search
CPC ............. A61B 17/24; A61B 17/12104; A61B 2017/3488; A61B 2018/00214;
(Continued)

(56) References Cited

U.S. PATENT DOCUMENTS

| 374,026 | A | * | 11/1887 | Williams | ......... | A61B 17/00234 |
| | | | | | | 604/2 |
| 1,381,829 | A | * | 6/1921 | Hartman | ................... | A61F 5/08 |
| | | | | | | 606/162 |

(Continued)

FOREIGN PATENT DOCUMENTS

| AU | 2008/201495 A1 | 10/2008 |
| DE | 101 05 592 A1 | 8/2002 |

(Continued)

OTHER PUBLICATIONS

Becker, D.G. (2003). "The Minimally Invasive, Endoscopic Approach to Sinus Surgery," *Journal of Long-Term Effects of Medical Implants* 13(3):207-221.
(Continued)

*Primary Examiner* — Scott J Medway
(74) *Attorney, Agent, or Firm* — Cooley LLP

(57) ABSTRACT

Described here are paranasal sinus devices for treating paranasal sinus conditions. The devices include a cavity member, ostial member, and nasal portion. One or more of the cavity member, ostial member, and nasal portion may deliver an active agent for sustained release to treat the paranasal sinus condition. Exemplary paranasal sinus conditions are sinus inflammation due to functional endoscopic sinus surgery (FESS) and rhinosinusitis.

12 Claims, 23 Drawing Sheets

Related U.S. Application Data continuation of application No. 11/398,342, filed on Apr. 4, 2006, now Pat. No. 8,025,635.

(60) Provisional application No. 60/668,569, filed on Apr. 4, 2005.

(51) Int. Cl.
| | | |
|---|---|---|
| *A61K 9/70* | (2006.01) | |
| *A61K 31/573* | (2006.01) | |
| *A61K 31/58* | (2006.01) | |
| *A61K 47/14* | (2017.01) | |
| *A61K 47/34* | (2017.01) | |
| *A61M 29/00* | (2006.01) | |
| *A61F 2/18* | (2006.01) | |
| *A61K 9/16* | (2006.01) | |

(52) U.S. Cl.
CPC .............. *A61K 31/58* (2013.01); *A61K 47/14* (2013.01); *A61K 47/34* (2013.01); *A61M 29/00* (2013.01); *A61F 2/186* (2013.01); *A61K 9/1647* (2013.01)

(58) Field of Classification Search
CPC .. A61M 2210/0618; A61M 2210/0681; A61M 25/04; A61F 2/82; A61F 2220/0016; A61F 2002/8486; A61F 2230/0067; A61F 2002/8483; A61F 2002/9511; A61F 2/00; A61F 2/02; A61F 2/18
See application file for complete search history.

(56) References Cited

U.S. PATENT DOCUMENTS

| | | | |
|---|---|---|---|
| 1,485,126 A * | 2/1924 | Schumacher | A46B 11/0055 401/185 |
| 1,520,908 A * | 12/1924 | Meyer | A61B 17/24 15/104.2 |
| 1,658,801 A * | 2/1928 | Condren | A61B 17/22 606/162 |
| 2,009,393 A | 7/1935 | Failla | |
| 2,096,162 A | 10/1937 | Daley | |
| 2,691,985 A | 10/1954 | Newsom | |
| 3,049,125 A | 8/1962 | Kriwkowitsch | |
| 3,473,165 A | 10/1969 | Gran et al. | |
| 3,502,078 A | 3/1970 | Hill et al. | |
| 3,570,494 A | 3/1971 | Gottschalk | |
| 3,583,391 A | 6/1971 | Cox et al. | |
| 3,766,924 A | 10/1973 | Pidgeon | |
| 3,800,788 A | 4/1974 | White | |
| 3,894,539 A | 7/1975 | Tallent | |
| 3,903,893 A | 9/1975 | Scheer | |
| 3,913,584 A | 10/1975 | Walchle et al. | |
| 4,094,303 A | 6/1978 | Johnston | |
| 4,245,652 A | 1/1981 | Kelly et al. | |
| 4,389,208 A | 6/1983 | LeVeen et al. | |
| 4,419,095 A | 12/1983 | Nebergall et al. | |
| D276,937 S | 12/1984 | Griggs | |
| 4,534,761 A | 8/1985 | Raible | |
| 4,580,568 A | 4/1986 | Gianturco | |
| 4,604,920 A | 8/1986 | Dupke | |
| 4,627,971 A | 12/1986 | Ayer | |
| 4,650,488 A | 3/1987 | Bays et al. | |
| 4,655,771 A | 4/1987 | Wallsten | |
| 4,704,126 A | 11/1987 | Baswell et al. | |
| 4,737,141 A | 4/1988 | Spits | |
| 4,744,792 A | 5/1988 | Sander et al. | |
| 4,753,636 A | 6/1988 | Free | |
| 4,793,351 A | 12/1988 | Landman et al. | |
| 4,886,493 A | 12/1989 | Yee | |
| 4,941,881 A | 7/1990 | Masters et al. | |
| 4,964,850 A | 10/1990 | Bouton et al. | |
| 5,000,957 A | 3/1991 | Eckenhoff et al. | |
| 5,011,474 A | 4/1991 | Brennan | |
| 5,035,706 A | 7/1991 | Giantureo et al. | |
| 5,062,829 A | 11/1991 | Pryor et al. | |
| 5,116,311 A | 5/1992 | Löfstedt | |
| 5,139,502 A | 8/1992 | Berg et al. | |
| 5,139,510 A | 8/1992 | Goldsmith, III et al. | |
| 5,139,832 A | 8/1992 | Hayashi et al. | |
| 5,167,614 A | 12/1992 | Tessmann et al. | |
| 5,189,110 A | 2/1993 | Ikematu et al. | |
| 5,217,484 A | 6/1993 | Marks | |
| 5,246,455 A | 9/1993 | Shikani | |
| 5,256,146 A | 10/1993 | Ensminger et al. | |
| 5,300,119 A | 4/1994 | Blom | |
| 5,312,813 A | 5/1994 | Costerton et al. | |
| 5,336,163 A | 8/1994 | DeMane et al. | |
| 5,342,296 A | 8/1994 | Persson et al. | |
| 5,344,426 A | 9/1994 | Lau et al. | |
| 5,348,553 A | 9/1994 | Whitney | |
| 5,350,580 A | 9/1994 | Muchow et al. | |
| 5,360,406 A | 11/1994 | Boykin et al. | |
| 5,391,179 A | 2/1995 | Mezzoli | |
| 5,443,498 A | 8/1995 | Fontaine | |
| 5,501,700 A | 3/1996 | Hirata | |
| 5,507,210 A | 4/1996 | Paramest | |
| 5,507,807 A | 4/1996 | Shippert | |
| 5,512,055 A | 4/1996 | Domb et al. | |
| 5,538,738 A | 7/1996 | Ritter et al. | |
| 5,540,712 A | 7/1996 | Kleshinski et al. | |
| 5,556,413 A | 9/1996 | Lam | |
| 5,632,762 A | 5/1997 | Myler | |
| 5,645,584 A | 7/1997 | Suyama | |
| 5,664,567 A | 9/1997 | Linder | |
| 5,672,179 A | 9/1997 | Garth et al. | |
| 5,693,065 A | 12/1997 | Rains, III | |
| 5,713,855 A | 2/1998 | Shippert | |
| 5,720,719 A | 2/1998 | Edwards et al. | |
| 5,746,224 A | 5/1998 | Edwards | |
| 5,749,921 A | 5/1998 | Lenker et al. | |
| 5,792,100 A | 8/1998 | Shantha | |
| 5,800,379 A | 9/1998 | Edwards | |
| 5,800,429 A | 9/1998 | Edwards | |
| 5,827,224 A | 10/1998 | Shippert | |
| 5,895,408 A * | 4/1999 | Pagan | A61B 17/24 604/1 |
| 5,899,878 A | 5/1999 | Glassman | |
| 5,928,190 A | 7/1999 | Davis | |
| 5,992,000 A | 11/1999 | Humphrey et al. | |
| 6,033,436 A | 3/2000 | Steinke et al. | |
| 6,054,122 A | 4/2000 | MacPhee et al. | |
| 6,063,102 A | 5/2000 | Morales | |
| 6,074,381 A | 6/2000 | Dinh et al. | |
| 6,082,990 A | 7/2000 | Jackson et al. | |
| 6,092,273 A | 7/2000 | Villareal | |
| 6,092,528 A | 7/2000 | Edwards | |
| 6,108,886 A | 8/2000 | Kimes et al. | |
| 6,113,641 A | 9/2000 | Leroy et al. | |
| 6,123,697 A | 9/2000 | Shippert | |
| 6,149,681 A | 11/2000 | Houser et al. | |
| 6,149,944 A | 11/2000 | Jeong et al. | |
| 6,152,946 A | 11/2000 | Broome et al. | |
| 6,180,848 B1 | 1/2001 | Flament et al. | |
| 6,190,353 B1 | 2/2001 | Makower et al. | |
| 6,195,225 B1 | 2/2001 | Komatsu et al. | |
| 6,200,335 B1 | 3/2001 | Igaki | |
| 6,214,036 B1 | 4/2001 | Letendre et al. | |
| 6,224,626 B1 | 5/2001 | Steinke | |
| 6,228,111 B1 | 5/2001 | Törmälä et al. | |
| 6,280,413 B1 | 8/2001 | Clark et al. | |
| 6,290,728 B1 | 9/2001 | Phelps et al. | |
| 6,297,227 B1 | 10/2001 | Johnson | |
| 6,302,875 B1 | 10/2001 | Makower et al. | |
| 6,306,084 B1 | 10/2001 | Pinczower | |
| 6,342,068 B1 | 1/2002 | Thompson | |
| 6,347,241 B2 | 2/2002 | Burbank et al. | |
| 6,350,465 B1 | 2/2002 | Jonnalagadda et al. | |
| 6,352,547 B1 | 3/2002 | Brown et al. | |
| 6,355,032 B1 | 3/2002 | Hovda et al. | |
| 6,375,615 B1 | 4/2002 | Flaherty et al. | |
| 6,386,197 B1 | 5/2002 | Miller | |

(56) References Cited

U.S. PATENT DOCUMENTS

| | | |
|---|---|---|
| 6,398,758 B1 | 6/2002 | Jacobsen et al. |
| 6,409,750 B1 * | 6/2002 | Hyodoh .................. A61F 2/07 |
| | | 623/1.1 |
| 6,436,112 B2 * | 8/2002 | Wensel ................ A61B 17/221 |
| | | 606/159 |
| 6,447,539 B1 | 9/2002 | Nelson et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,605,111 B2 * | 8/2003 | Bose ................ A61B 17/12022 |
| | | 606/153 |
| 6,605,294 B2 | 8/2003 | Sawhney |
| 6,606,995 B1 | 8/2003 | Sadek et al. |
| 6,618,921 B1 | 9/2003 | Thornton |
| 6,648,849 B2 | 11/2003 | Tenhuisen et al. |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |
| 7,195,016 B2 | 3/2007 | Loyd et al. |
| 7,225,518 B2 | 6/2007 | Eidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,594,928 B2 | 9/2009 | Headley, Jr. et al. |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 | 11/2013 | Eaton et al. |
| 8,585,731 B2 | 11/2013 | Abbate et al. |
| 8,585,753 B2 | 11/2013 | Scanlon et al. |
| 8,721,591 B2 | 5/2014 | Chang et al. |
| 8,740,029 B2 | 6/2014 | Barnoski et al. |
| 8,740,839 B2 | 6/2014 | Eaton et al. |
| 8,740,929 B2 | 6/2014 | Gopferich et al. |
| 8,763,222 B2 | 7/2014 | Abbate et al. |
| 8,802,131 B2 | 8/2014 | Arensdorf et al. |
| 8,858,974 B2 | 10/2014 | Eaton et al. |
| 8,986,341 B2 | 3/2015 | Abbate et al. |
| 9,101,689 B2 | 8/2015 | Hossainy et al. |
| 9,585,681 B2 | 3/2017 | Eaton et al. |
| 9,782,283 B2 | 10/2017 | Abbate et al. |
| 10,010,651 B2 | 7/2018 | Eaton et al. |
| 10,471,185 B2 | 11/2019 | Eaton et al. |
| 2002/0022048 A1 | 2/2002 | Bromberg et al. |
| 2002/0037919 A1 | 3/2002 | Hunter |
| 2002/0051793 A1 | 5/2002 | Drabick |
| 2002/0051845 A1 | 5/2002 | Mehta et al. |
| 2002/0055746 A1 | 5/2002 | Burke et al. |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0033001 A1 | 2/2003 | Igaki |
| 2003/0040771 A1 | 2/2003 | Hyodoh et al. |
| 2003/0040790 A1 | 2/2003 | Furst |
| 2003/0055488 A1 | 3/2003 | Igaki |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0109837 A1 * | 6/2003 | Mcbride-Sakal ......................... |
| | | A61B 17/320758 |
| | | 604/267 |
| 2003/0125774 A1 | 7/2003 | Salo |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0158598 A1 | 8/2003 | Ashton |
| 2003/0195459 A1 | 10/2003 | Shippert |
| 2003/0203030 A1 | 10/2003 | Ashton et al. |
| 2003/0206864 A1 * | 11/2003 | Mangin .............. A61K 47/6925 |
| | | 424/9.52 |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0091543 A1 * | 5/2004 | Bell ................ A61B 17/12022 |
| | | 424/489 |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043783 A1 | 2/2005 | Amis et al. |
| 2005/0119725 A1 | 6/2005 | Wang et al. |
| 2005/0124560 A1 | 6/2005 | Sung et al. |
| 2005/0131460 A1 | 6/2005 | Gilford |
| 2005/0131514 A1 | 6/2005 | Hijlkema et al. |

(56) References Cited

U.S. PATENT DOCUMENTS

| | | |
|---|---|---|
| 2005/0131524 A1 | 6/2005 | Majercak et al. |
| 2005/0131525 A1 | 6/2005 | Hartley |
| 2005/0143817 A1 | 6/2005 | Hunter et al. |
| 2005/0163821 A1 | 7/2005 | Sung et al. |
| 2005/0165347 A1 | 7/2005 | Bardy |
| 2005/0203605 A1 | 9/2005 | Dolan |
| 2005/0229670 A1 | 10/2005 | Perreault |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0025849 A1 | 2/2006 | Kaplan et al. |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |
| 2006/0247499 A1 | 11/2006 | Butler et al. |
| 2006/0265042 A1 | 11/2006 | Catanese, III et al. |
| 2006/0276871 A1 | 12/2006 | Lamson et al. |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0129751 A1 | 6/2007 | Muni et al. |
| 2007/0135789 A1 | 6/2007 | Chang et al. |
| 2007/0156211 A1 | 7/2007 | Ferren et al. |
| 2007/0156229 A1 | 7/2007 | Park |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yuri et al. |
| 2007/0270941 A1 | 11/2007 | Headley et al. |
| 2007/0282305 A1 | 12/2007 | Goldfarb et al. |
| 2007/0289677 A1 | 12/2007 | Ma et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0056709 A1 | 3/2009 | Worsoff |
| 2009/0093823 A1 | 4/2009 | Chang et al. |
| 2009/0177272 A1* | 7/2009 | Abbate ............... A61K 9/70 623/1.42 |
| 2009/0187098 A1 | 7/2009 | Makower et al. |
| 2009/0198179 A1 | 8/2009 | Abbate et al. |
| 2009/0198216 A1 | 8/2009 | Muni et al. |
| 2009/0240112 A1 | 9/2009 | Goldfarb et al. |
| 2009/0312745 A1 | 12/2009 | Goldfarb et al. |
| 2011/0004192 A1 | 1/2011 | Eaton et al. |
| 2011/0021986 A1 | 1/2011 | Zamboni |
| 2011/0167964 A1 | 7/2011 | Price |
| 2012/0101429 A1 | 4/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 9/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0074065 A1 | 3/2014 | Muni et al. |
| 2014/0079755 A1 | 3/2014 | Eaton et al. |
| 2014/0107615 A1 | 4/2014 | Doshi et al. |
| 2014/0283349 A1 | 9/2014 | Abbate et al. |
| 2014/0324025 A1 | 10/2014 | Arensdorf et al. |
| 2015/0081017 A1 | 3/2015 | Abbate et al. |
| 2016/0287854 A1 | 10/2016 | Eaton et al. |
| 2019/0143087 A1 | 5/2019 | Eaton et al. |
| 2020/0108181 A1 | 4/2020 | Eaton et al. |
| 2020/0206391 A1 | 7/2020 | Eaton et al. |

FOREIGN PATENT DOCUMENTS

| | | |
|---|---|---|
| EP | 0 423 916 A1 | 4/1991 |
| EP | 0 761 251 A1 | 3/1997 |
| EP | 0 938 880 A2 | 9/1999 |
| EP | 1 415 671 A1 | 5/2004 |
| EP | 1 870 057 A1 | 12/2007 |
| JP | 2-500521 A | 2/1990 |
| JP | H04-25755 A | 2/1992 |
| JP | H-6-5800 Y2 | 2/1994 |
| JP | 6-506672 A | 7/1994 |
| JP | 6-329542 A | 11/1994 |
| JP | 8-117326 A | 5/1996 |

(56) References Cited

FOREIGN PATENT DOCUMENTS

| | | |
|---|---|---|
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |
| WO | WO-01/02024 C1 | 1/2001 |
| WO | WO-01/26658 A2 | 4/2001 |
| WO | WO-01/26658 A3 | 4/2001 |
| WO | WO-01/30411 A1 | 5/2001 |
| WO | WO-01/95834 A1 | 12/2001 |
| WO | WO-03/090818 A2 | 11/2003 |
| WO | WO-03/090818 A3 | 11/2003 |
| WO | WO-03/099359 A1 | 12/2003 |
| WO | WO-2004/016200 A1 | 2/2004 |
| WO | WO-2004/082525 A2 | 9/2004 |
| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/067451 A2 | 6/2007 |
| WO | WO-2007/067451 A3 | 6/2007 |
| WO | WO-2007/134215 A2 | 11/2007 |
| WO | WO-2007/134215 A3 | 11/2007 |
| WO | WO-2007/139668 A2 | 12/2007 |
| WO | WO-2007/139668 A3 | 12/2007 |
| WO | WO-2008/008389 A2 | 1/2008 |
| WO | WO-2008/008389 A3 | 1/2008 |
| WO | WO-2008/033533 A2 | 3/2008 |
| WO | WO-2008/033533 A3 | 3/2008 |
| WO | WO-2008/051453 A2 | 5/2008 |
| WO | WO-2008/051453 A3 | 5/2008 |
| WO | WO-2008/051881 A2 | 5/2008 |
| WO | WO-2008/051881 A3 | 5/2008 |
| WO | WO-2008/054655 A2 | 5/2008 |
| WO | WO-2008/054655 A3 | 5/2008 |
| WO | WO-2008/070996 A1 | 6/2008 |
| WO | WO-2008/154143 A2 | 12/2008 |
| WO | WO-2008/154143 A3 | 12/2008 |
| WO | WO-2009/079418 A3 | 12/2008 |
| WO | WO-2009/079418 A2 | 6/2009 |
| WO | WO-2010/014834 A1 | 2/2010 |
| WO | WO-2012/083594 A1 | 6/2012 |
| WO | WO-2012/107229 A1 | 8/2012 |
| WO | WO-2013/158337 A1 | 10/2013 |

OTHER PUBLICATIONS

Bolliger, C.T. et al. (1999). "Evaluation of a New Self-Expandable Silicone Stent in an Experimental Tracheal Stenosis," *Chest* 115:496-501.
Eberhart, R.C. et al. (2003). "Bioresorbable Polymeric Stents: Current Status and Future Promise," *J. Biomater. Sci. Polymer Edn.* 14(4):299-312.
European Search Report dated Feb. 21, 2011, for EP Patent Application No. 10 011 116.0 filed on Apr. 4, 2006, 8 pages.
European Search Report dated Feb. 21, 2011, for EP Patent Application No. 10 011 117.8 filed on Apr. 4, 2006, 8 pages.
European Search Report dated Feb. 21, 2011, for EP Patent Application No. 10 011 118.6 filed on Apr. 4, 2006, 8 pages.
Extended European Search Report dated Jun. 18, 2015, for EP Patent Application No. 08 863 327.6, filed on Jul. 16, 2010, 8 pages.
Extended European Search Report dated Jun. 26, 2015, for European Patent Application No. 09 803 604.9, filed on Jul. 30, 2009, 7 pages.
Final Office Action dated Jan. 8, 2009, for U.S. Appl. No. 10/800,162, filed Mar. 12, 2004, 5 pages.
Final Office Action dated Jul. 22, 2009, for U.S. Appl. No. 11/398,342, filed Apr. 4, 2006, 8 pages.
Final Office Action dated Jul. 8, 2010, for U.S. Appl. No. 11/398,342, filed Apr. 4, 2006, 7 pages.
Final Office Action dated Aug. 18, 2010, for U.S. Appl. No. 11/775,157, filed Jul. 9, 2007, 12 pages.
Final Office Action dated Jan. 27, 2011, for U.S. Appl. No. 12/479,794, filed Jun. 6, 2009, 6 pages.
Final Office Action dated Nov. 28, 2011, for U.S. Appl. No. 12/883,071, filed Sep. 15, 2010, 7 pages.
Final Office Action dated Mar. 1, 2012, for U.S. Appl. No. 12/270,695, filed Nov. 13, 2008, 26 pages.
Final Office Action dated Apr. 12, 2012, for U.S. Appl. No. 12/883,087, filed Sep. 15, 2010, 7 pages.
Final Office Action dated Apr. 16, 2012, for U.S. Appl. No. 12/334,373, filed Dec. 12, 2008, 7 pages.
Final Office Action dated May 29, 2012, for U.S. Appl. No. 12/334,382, filed Dec. 12, 2008, 7 pages.
Final Office Action dated Mar. 6, 2013, for U.S. Appl. No. 13/341,732, filed Dec. 30, 2011, 7 pages.
Final Office Action dated May 30, 2013, for U.S. Appl. No. 12/541,840, filed Aug. 14, 2009, 11 pages.
Final Office Action dated Sep. 10, 2013, for U.S. Appl. No. 12/334,395, filed Dec. 12, 2008, 8 pages.
Final Office Action dated May 5, 2014 for U.S. Appl. No. 12/883,087, filed Sep. 15, 2010, 10 pages.
Final Office Action dated May 19, 2014, for U.S. Appl. No. 13/341,732, filed Dec. 30, 2011, 7 pages.
Final Office Action dated Sep. 17, 2014, for U.S. Appl. No. 12/334,395, filed Dec. 12, 2008, 10 pages.
Final Office Action dated Feb. 12, 2015, for U.S. Appl. No. 13/341,732, filed Dec. 30, 2011, 8 pages.
Final Office Action dated Oct. 20, 2015, for U.S. Appl. No. 12/883,087, filed Sep. 15, 2010, 15 pages.
Final Office Action dated Feb. 8, 2016, for U.S. Appl. No. 12/334,395, filed Dec. 12, 2008, 18 pages.
Final Office Action dated Jun. 29, 2016, for U.S. Appl. No. 14/327,100, filed Jul. 9, 2014, 17 pages.
Final Office Action dated Sep. 16, 2016, for U.S. Appl. No. 14/081,974, filed Nov. 15, 2013, 12 pages.
Final Office Action dated Sep. 20, 2016, for U.S. Appl. No. 14/550,634, filed Nov. 21, 2014, 11 pages.
Hietala, E-M. et al. (2001). "Biodegradation of the Copolymeric Polylactide Stent," *Journal of Vascular Research* 38:361-369.
Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.
Hughes, J.P. et al. (Apr. 2004). "Use of a Ureteric Pigtail Stent as a Self-Retaining Frontal Sinus Stent," *The Journal of Laryngology & Otology* 118:299-301.
International Search Report dated Feb. 24, 2006 for PCT Application No. PCT/US04/07828 filed Mar. 12, 2004, 1 page.
International Search Report dated Sep. 11, 2006, for PCT Patent Application No. PCT/US2006/012484 filed on Apr. 4, 2006, 6 pages.
International Search Report dated Mar. 19, 2008, for PCT Patent Application No. PCT/US2007/015813, filed on Jul. 10, 2007, 3 pages.
International Search Report dated Mar. 11, 2009, for PCT Application No. PCT/US2008/86178, filed on Dec. 12, 2008, 3 pages.
International Search Report dated Sep. 28, 2009, for PCT Application No. PCT/US2009/052287, filed on Jul. 30, 2009, 2 pages.
Laaksovirta, S. (Aug. 22, 2003). *Biodegradable, Self-Reinforced, Self-Expandable Lactic and Glycolic Acid (SR-PLGA 80/20) Copolymer Spiral Prostatic Stent: Analysis of Mechanical and Biological Properties and Clinical Results*, Academic Dissertation, Medical School of the University of Tampere, 79 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii*, 2 pages.
Lavigne, F. et al. (May 2002). "Intrasinus Administration of Topical Budesonide to Allergic Patients With Chronic Rhinosinusitis Following Surgery," *The Laryngoscope* 112, 7 pages.

(56) References Cited

OTHER PUBLICATIONS

Min, Y-G. et al. (1995). "Application of Polylactic Acid Polymer in the Treatment of Acute Maxillary Sinusitis in Rabbits," *Acta Otolaryngol.* 115:548-552.

Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.

Mirza, S. et al. (Dec. 2000). "A Simple and Effective Frontal Sinus Stent," *The Journal of Laryngology & Otology* 114:955-956.

Mitty, H. et al. (1988). "Experience with a New Ureteral Stent Made of a Biocompatible Copolymer," *Radiology* 168:557-559.

Murphy, J.G. et al. (1992). "Percutaneous Polymeric Stents in Porcine Coronary Arteries: Initial Experience With Polyethylene Terephthalate Stents," *Circulation* 86:1596-1604.

Nguyen, K.T. et al. (2004). "Biomaterials and Stent Technology," Chapter 5 in *Tissue Engineering and Novel Delivery Systems*, 24 pages.

Non-Final Office Action dated Jun. 6, 2008, for U.S. Appl. No. 10/800,162, filed Mar. 12, 2004, 5 pages.

Non-Final Office Action dated Nov. 25, 2008, for U.S. Appl. No. 11/398,342, filed Apr. 4, 2006, 10 pages.

Non-Final Office Action dated Sep. 22, 2009, for U.S. Appl. No. 12/419,927, filed Apr. 7, 2009, 4 pages.

Non-Final Office Action dated Sep. 22, 2009, for U.S. Appl. No. 12/419,943, filed Apr. 7, 2009, 5 pages.

Non-Final Office Action dated Sep. 22, 2009, for U.S. Appl. No. 12/419,930, filed Apr. 7, 2007, 4 pages.

Non-Final Office Action dated Sep. 22, 2009, for U.S. Appl. No. 12/419,937, filed Apr. 7, 2009, 4 pages.

Non-Final Office Action dated Sep. 22, 2009, for U.S. Appl. No. 12/419,925, filed Apr. 7, 2009, 4 pages.

Non-Final Office Action dated Nov. 13, 2009, for U.S. Appl. No. 11/398,342, filed Apr. 4, 2006, 9 pages.

Non-Final Office Action dated Dec. 9, 2009, for U.S. Appl. No. 11/775,157, filed Jul. 9, 2007, 12 pages.

Non-Final Office Action dated Jul. 1, 2010, for U.S. Appl. No. 12/479,794, filed Jun. 6, 2009, 5 pages.

Non-Final Office Action dated Sep. 10, 2010, for U.S. Appl. No. 12/437,374, filed May 7, 2009, 8 pages.

Non-Final Office Action dated Nov. 12, 2010, for U.S. Appl. No. 11/398,342, filed Apr. 4, 2006, 8 pages.

Non-Final Office Action dated Nov. 23, 2010, for U.S. Appl. No. 12/258,277, filed Oct. 24, 2008, 9 pages.

Non-Final Office Action dated Nov. 23, 2010, for U.S. Appl. No. 12/258,282, filed Oct. 24, 2008, 7 pages.

Non-Final Office Action dated Nov. 24, 2010, for U.S. Appl. No. 12/883,090, filed Sep. 15, 2010, 7 pages.

Non-Final Office Action dated Nov. 24, 2010, for U.S. Appl. No. 12/883,056, filed Sep. 15, 2010, 7 pages.

Non-Final Office Action dated Nov. 24, 2010, for U.S. Appl. No. 12/883,079, filed Sep. 15, 2010, 8 pages.

Non-Final Office Action dated Mar. 22, 2011, for U.S. Appl. No. 12/883,071, filed Sep. 15, 2010, 8 pages.

Non-Final Office Action dated May 13, 2011, for U.S. Appl. No. 12/883,087, filed Sep. 15, 2010, 7 pages.

Non-Final Office Action dated Jun. 14, 2011, for U.S. Appl. No. 12/437,374, filed May 7, 2009, 8 pages.

Non-Final Office Action dated Jun. 21, 2011, for U.S. Appl. No. 12/270,695, filed Nov. 13, 2008, 24 pages.

Non-Final Office Action dated Jul. 13, 2011, for U.S. Appl. No. 12/334,373, filed Dec. 12, 2008, 8 pages.

Non-Final Office Action dated Sep. 26, 2011, for U.S. Appl. No. 12/334,382, filed Dec. 12, 2008, 7 pages.

Non-Final Office Action dated May 11, 2012, for U.S. Appl. No. 12/883,071, filed Sep. 15, 2010, 7 pages.

Non-Final Office Action dated Jun. 7, 2012, for U.S. Appl. No. 12/334,395, filed Dec. 12, 2008, 7 pages.

Non-Final Office Action dated Oct. 18, 2012, for U.S. Appl. No. 12/541,840, filed Aug. 14, 2009, 10 pages.

Non-Final Office Action dated Mar. 15, 2013, for U.S. Appl. No. 12/512,855, filed Jul. 30, 2009, 10 pages.

Non-Final Office Action dated Sep. 12, 2013 for U.S. Appl. No. 13/341,732, filed Dec. 30, 2011, 5 pages.

Non-Final Office Action dated Sep. 23, 2013, for U.S. Appl. No. 12/883,087, filed Sep. 15, 2010, 7 pages.

Non-Final Office Action dated Feb. 27, 2014, for U.S. Appl. No. 12/270,695, filed Nov. 13, 2008, 7 pages.

Non-Final Office Action dated Apr. 16, 2014, for U.S. Appl. No. 12/334,395, filed Dec. 12, 2008, 9 pages.

Non-Final Office Action dated Jun. 12, 2014, for U.S. Appl. No. 14/082,010, filed Nov. 15, 2013, 6 pages.

Non-Final Office Action dated Sep. 23, 2014, for U.S. Appl. No. 13/341,732, filed Dec. 30, 2011, 8 pages.

Non-Final Office Action dated Mar. 20, 2015, for U.S. Appl. No. 12/883,087, filed Sep. 15, 2010, 11 pages.

Non-Final Office Action dated May 8, 2015, for U.S. Appl. No. 12/334,395, filed Dec. 12, 2008, 11 pages.

Non-Final Office Action dated Sep. 10, 2015, for U.S. Appl. No. 13/341,732, filed Dec. 30, 2011, 6 pages.

Non-Final Office Action dated Nov. 12, 2015, for U.S. Appl. No. 14/327,100, filed Jul. 9, 2014, 12 pages.

Non-Final Office Action dated Feb. 5, 2016, for U.S. Appl. No. 12/883,087, filed Sep. 15, 2010, 12 pages.

Non-Final Office Action dated Feb. 5, 2016, for U.S. Appl. No. 14/081,974, filed Nov. 15, 2013, 12 pages.

Non-Final Office Action dated Apr. 28, 2016, for U.S. Appl. No. 14/550,634, filed Nov. 21, 2014, 10 pages.

Non-Final Office Action dated Aug. 11, 2016, for U.S. Appl. No. 12/334,395, filed Dec. 12, 2008, 12 pages.

Non-Final Office Action dated Mar. 20, 2017, for U.S. Appl. No. 14/298,715, filed Jun. 6, 2014, 7 pages.

Non-Final Office Action dated Jun. 29, 2017, for U.S. Appl. No. 14/081,974, filed Nov. 15, 2013, 15 pages.

Notice of Allowance dated Dec. 23, 2009, for U.S. Appl. No. 12/419,925, filed Apr. 7, 2009, 2 pages.

Notice of Allowance dated Dec. 23, 2009, for U.S. Appl. No. 12/419,943, filed Apr. 7, 2009, 2 pages.

Notice of Allowance dated Dec. 24, 2009, for U.S. Appl. No. 12/419,927, filed Apr. 7, 2009, 2 pages.

Notice of Allowance dated Jan. 19, 2010, for U.S. Appl. No. 12/419,930, filed Apr. 7, 2009, 2 pages.

Notice of Allowance dated Feb. 2, 2010, for U.S. Appl. No. 12/419,937, filed Apr. 7, 2009, 2 pages.

Notice of Allowance dated Mar. 18, 2011, for U.S. Appl. No. 12/258,277, filed Oct. 24, 2008, 7 pages.

Notice of Allowance dated Mar. 21, 2011, for U.S. Appl. No. 12/258,282, filed Oct. 24, 2008, 8 pages.

Notice of Allowance dated Mar. 21, 2011, for U.S. Appl. No. 12/883,059, filed Sep. 15, 2010, 10 pages.

Notice of Allowance dated Mar. 23, 2011, for U.S. Appl. No. 12/883,079, filed Sep. 15, 2010, 9 pages.

Notice of Allowance dated Mar. 25, 2011 for U.S. Appl. No. 12/883,090, filed Sep. 15, 2010, 8 pages.

Notice of Allowance dated Mar. 25, 2011, for U.S. Appl. No. 12/883,056, filed Sep. 15, 2010, 8 pages.

Notice of Allowance dated Jul. 13, 2011, for U.S. Appl. No. 11/398,342, filed Apr. 4, 2006, 7 pages.

Notice of Allowance dated Nov. 9, 2011, for U.S. Appl. No. 12/479,794, filed Jun. 6, 2009, 7 pages.

Notice of Allowance dated Aug. 20, 2012, for U.S. Appl. No. 12/437,374, filed May 7, 2009, 8 pages.

Notice of Allowance dated Nov. 2, 2012, for U.S. Appl. No. 11/775,157, filed Jul. 9, 2007, 8 pages.

Notice of Allowance dated May 22, 2013, for U.S. Appl. No. 11/775,157, filed Jul. 9, 2007, 10 pages.

Notice of Allowance dated Jul. 15, 2013, for U.S. Appl. No. 12/334,382, filed Dec. 12, 2008, 9 pages.

Notice of Allowance dated Jul. 30, 2013, for U.S. Appl. No. 12/334,373, filed Dec. 12, 2008, 10 pages.

(56) References Cited

OTHER PUBLICATIONS

Notice of Allowance dated Sep. 19, 2013, for U.S. Appl. No. 12/883,071, filed Sep. 15, 2010, 6 pages.
Notice of Allowance dated Nov. 27, 2013, for U.S. Appl. No. 12/512,855, filed Jul. 30, 2009, 9 pages.
Notice of Allowance dated Jan. 21, 2014, for U.S. Appl. No. 12/883,071, filed Sep. 15, 2010, 6 pages.
Notice of Allowance dated Feb. 19, 2014, for U.S. Appl. No. 12/512,855, filed Jul. 30, 2009, 7 pages.
Notice of Allowance dated Apr. 8, 2014, for U.S. Appl. No. 12/541,840, filed Aug. 14, 2009, 8 pages.
Notice of Allowance (Corrected) dated May 29, 2014, for U.S. Appl. No. 12/512,855, filed Jul. 30, 2009, 4 pages.
Notice of Allowance dated Jun. 12, 2014, for U.S. Appl. No. 12/270,695, filed Nov. 13, 2008, 7 pages.
Notice of Allowance dated Nov. 12, 2014, for U.S. Appl. No. 14/082,010, filed Nov. 15, 2013, 5 pages.
Notice of Allowance dated Feb. 17, 2015, for U.S. Appl. No. 14/082,010, filed Nov. 15, 2013, 5 pages.
Notice of Allowance dated Nov. 18, 2016, for U.S. Appl. No. 14/298,715, filed Jun. 6, 2014, 8 pages.
Notice of Allowance dated Jun. 20, 2017, for U.S. Appl. No. 14/298,715, filed Jun. 6, 2014, 5 pages.
Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Parviainen, M. et al. (2000). "A New Biodegradable Stent for the Pancreaticojejunal Anastomosis After Pancreaticoduodenal Resection: In Vitro Examination and Pilot Experiences in Humans," *Pancreas* 21(1):14-21.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Piskunov, S. et al. (1993). "The Prolongation of Drug Action in the Treatment of Diseases of the Nose and Paranasal Sinuses," *Rhinology* 31:33-36.
Roumestan, C. et al. (2003). "Fluticasone Propionate and Mometasone Furoate Have Equivalent Transcriptional Potencies," *Clinical and Experimental Allergy* 33: 895-901.
Shikani, A.H. (Aug. 1996). "Use of Antibiotics for Expansion of the Merocel® Packing Following Endoscopic Sinus Surgery," *ENT Journal* 75(8):524-528.
Su, S-H. et al. (2003). "Expandable Bioresorbable Endovascular Stent. I. Fabrication and Properties," *Annals of Biomedical Engineering* 31:667-677.
Supplementary European Search Report dated Nov. 9, 2010, for European Patent Application No. 04 720 509.1, filed on Mar. 12, 2004, 3 pages.
Tamai, H. et al. (1999). "A Biodegradable Ploy-/-lactic Acid Coronary Stent in the Porcine Coronary Artery," *Journal of Interventional Cardiology* 12(6):443-450.

Thierry, B. et al. (Nov./Dec. 2003, e-pub. Oct. 7, 2003). "Bioactive Coatings of Endovascular Stents Based on Polyelectrolyte Multilayers," *Biomacromolecules* 4(6):1564-1571.
Third Party Submission under 37 CFR 1.290 submitted Oct. 11, 2014, against U.S. Appl. No. 14/081,974, filed Nov. 15, 2013, 8 pages.
Toffel, P.N. (Mar. 2001). "The Balanced Philosophy of Secure Multimodal Endoscopic Sinus Surgery with Adjunct Use of Middle Meatal Stenting and Middle Turbinate Modification," *Operative Techniques in Otolaryngology—Head and Neck Surgery* 12(1):40-45.
Vogt, F. et al. (2004, e-pub. Jul. 20, 2004). "Long-Term Assessment of a Novel Biodegradable Paclitaxel-Eluting Coronary Polylactide Stent," *European Heart Journal* 25:1330-1340.
Written Opinion of the International Searching Authority dated Sep. 11, 2006, for PCT Patent Application No. PCT/US2006/012484, filed on Apr. 4, 2006, 11 pages.
Written Opinion of the International Searching Authority dated Sep. 28, 2009, for PCT Application No. PCT/US2009/052287, filed on Jul. 30, 2009, 9 pages.
Written Opinion of the International Searching Authority dated Feb. 24, 2006 for PCT Application No. PCT/US04/07828, filed Mar. 12, 2004, 3 pages.
Written Opinion of the International Searching Authority dated Mar. 19, 2008, for PCT Patent Application No. PCT/US2007/015813, filed on Jul. 10, 2007, 7 pages.
Written Opinion of the International Searching Authority dated Apr. 16, 2009, for PCT Application No. PCT/US2008/86718, filed on Dec. 12, 2008, 13 pages.
Corrected Notice of Allowability dated May 2, 2018, for U.S. Appl. No. 14/081,974, filed Nov. 15, 2013, 2 pages.
Final Office Action dated Nov. 30, 2017, for U.S. Appl. No. 14/081,974, filed Nov. 15, 2013, 11 pages.
Non-Final Office Action dated Dec. 13, 2017, for U.S. Appl. No. 15/062,616, filed Mar. 7, 2016, 13 pages.
Notice of Allowance dated Apr. 6, 2018, for U.S. Appl. No. 14/081,974, filed Nov. 15, 2013, 9 pages.
U.S. Appl. No. 16/007,327, filed Jun. 13, 2018, by Eaton et al.
U.S. Appl. No. 16/021,659, filed Jun. 28, 2018, by Eaton et al.
Non-Final Office Action dated Jul. 25, 2019, for U.S. Appl. No. 16/021,659, filed Jun. 28, 2018, 21 pages.
Non-Final Office Action dated Feb. 10, 2020, for U.S. Appl. No. 16/007,327, filed Jun. 13, 2018, 10 pages.
Notice of Allowance dated Sep. 12, 2019, for U.S. Appl. No. 16/021,659, filed Jun. 28, 2018, 10 pages.
Final Office Action dated Aug. 19, 2020, for U.S. Appl. No. 16/007,327, filed Jun. 13, 2018, 12 pages.
Extended European Search Report dated Feb. 8, 2021, for European Patent Application No. 20 203 807.1, filed on Jul. 30, 2009, 9 pages.
Final Office Action dated Apr. 16, 2021, for U.S. Appl. No. 17/075,572, filed Oct. 20, 2020, 2021, 12 pages.
Non-Final Office Action dated Dec. 10, 2020, for U.S. Appl. No. 16/007,327, filed Jun. 13, 2018, 13 pages.
Non-Final Office Action dated Dec. 22, 2020, for U.S. Appl. No. 17/075,572, filed Oct. 20, 2020, 9 pages.

\* cited by examiner

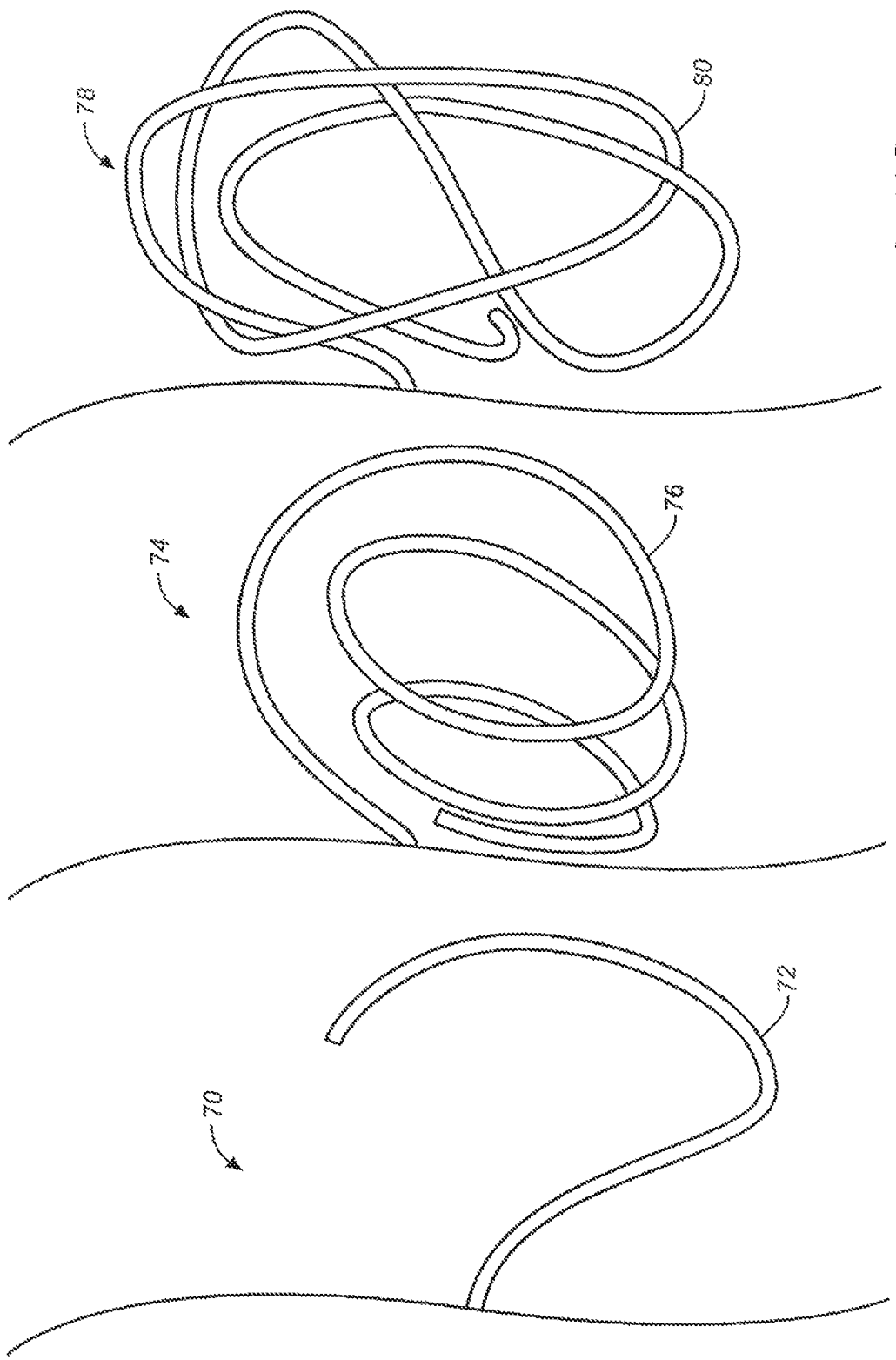

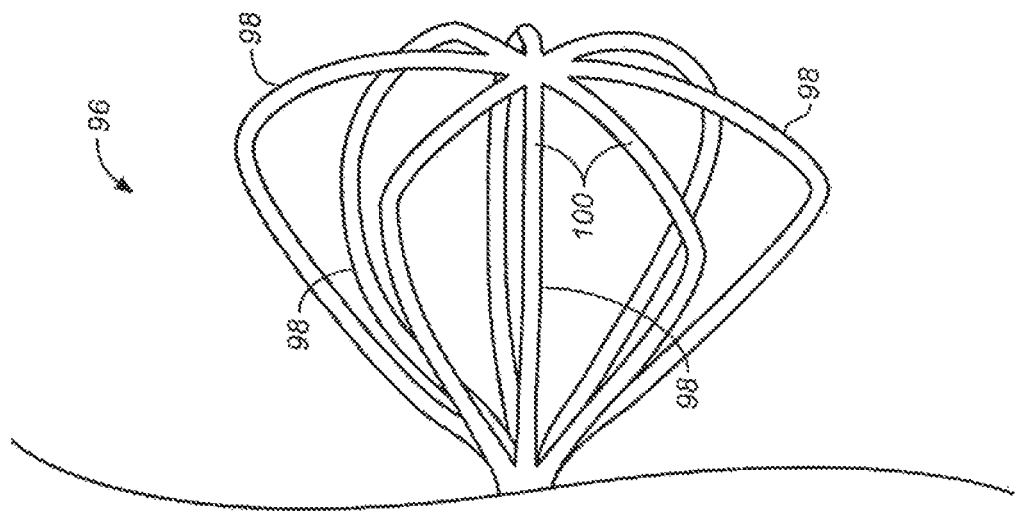
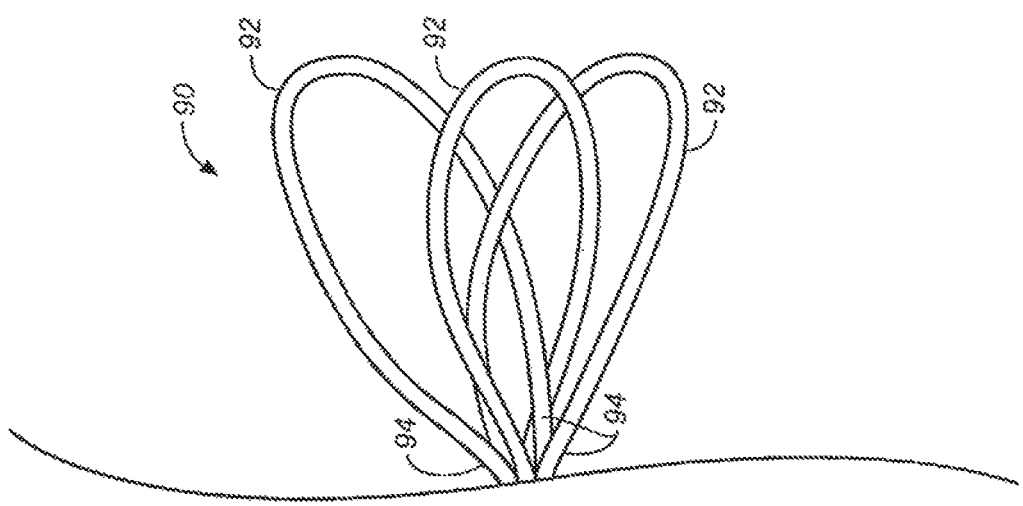
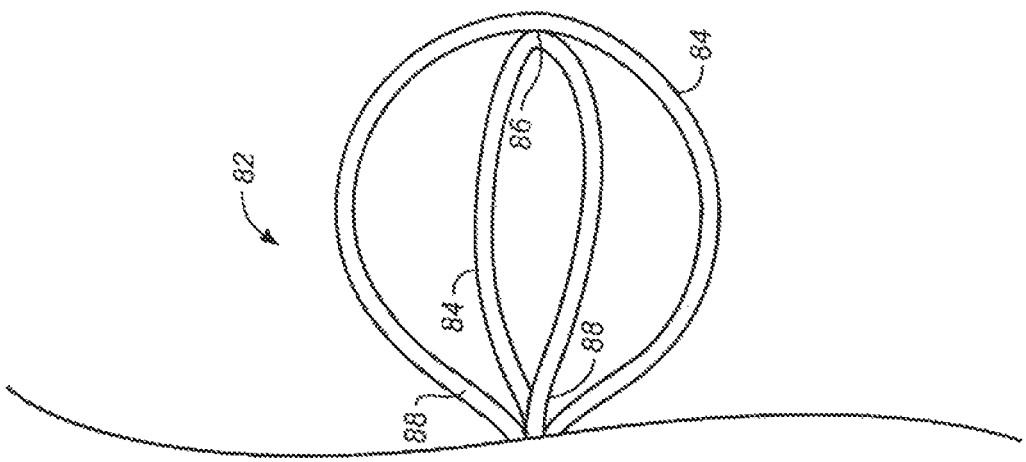

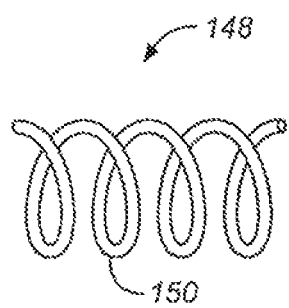
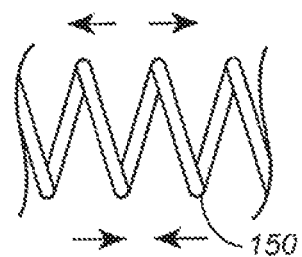
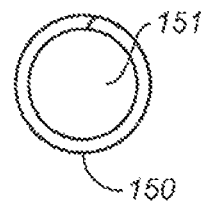
FIG. 8A    FIG. 8B    FIG. 8C
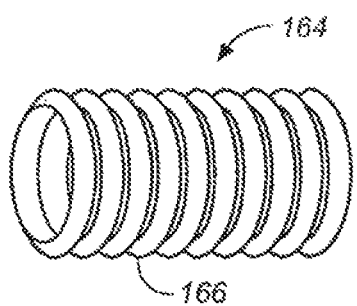
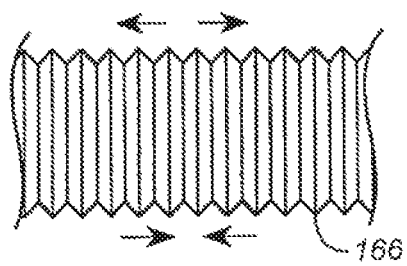
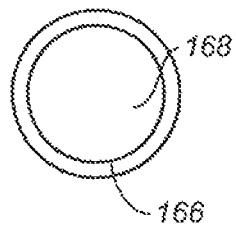
FIG. 9A    FIG. 9B    FIG. 9C
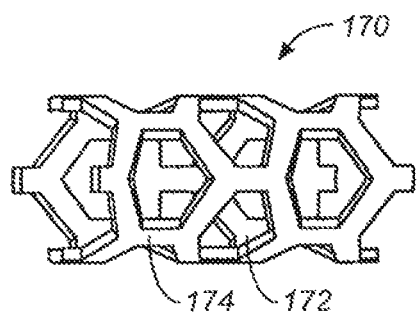
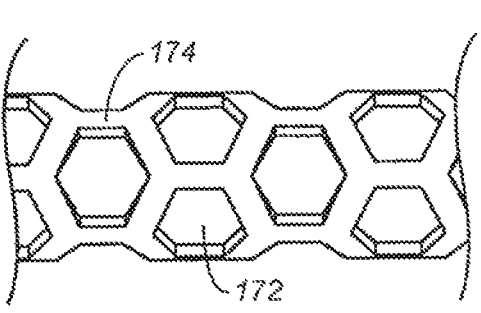
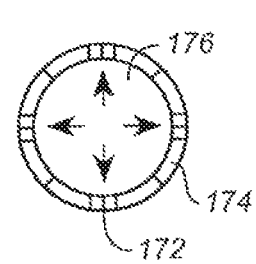
FIG. 10A    FIG. 10B    FIG. 10C

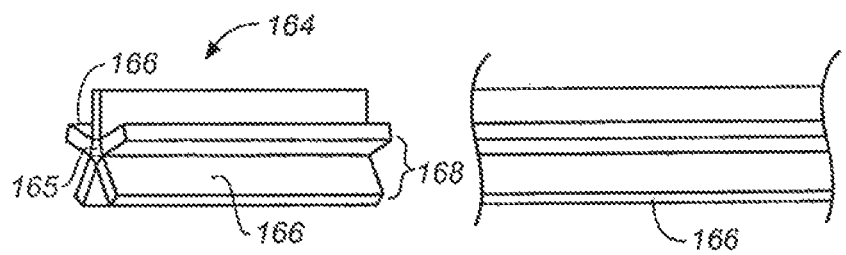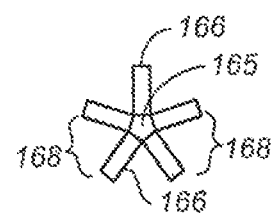
FIG. 11A  FIG. 11B  FIG. 11C
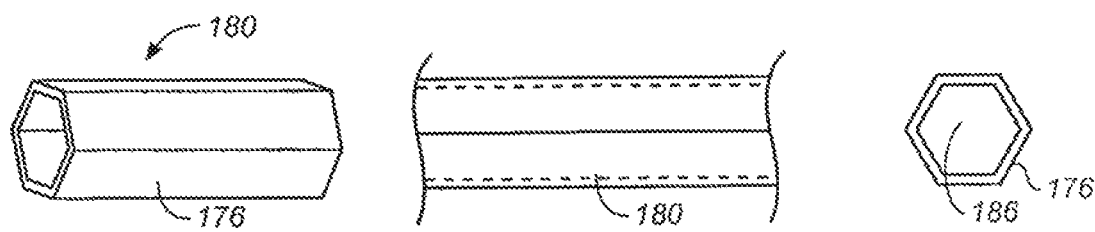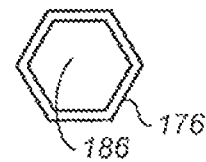
FIG. 12A  FIG. 12B  FIG. 12C
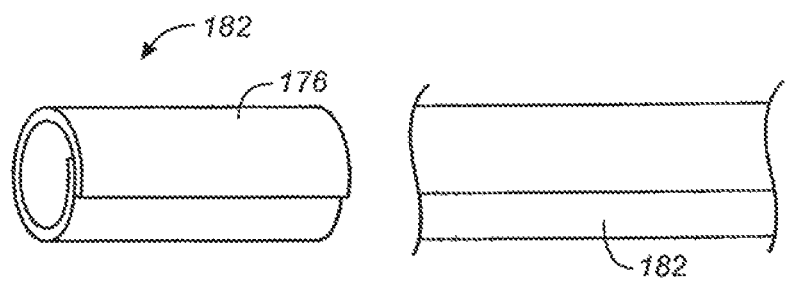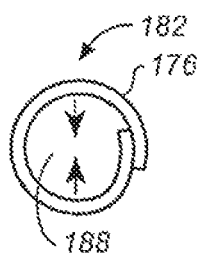
FIG. 13A  FIG. 13B  FIG. 13C

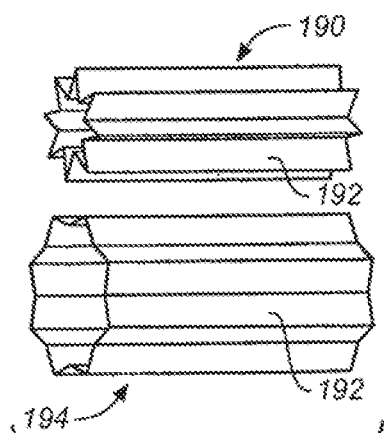 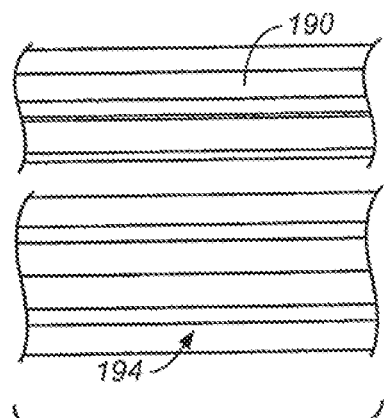 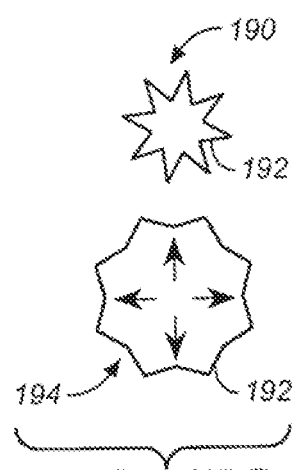
FIG. 17A  FIG. 17B  FIG. 17C
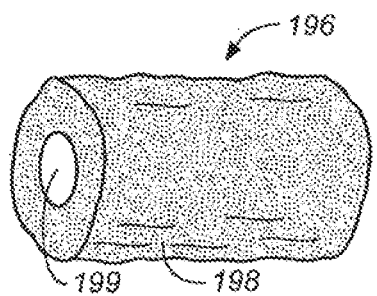 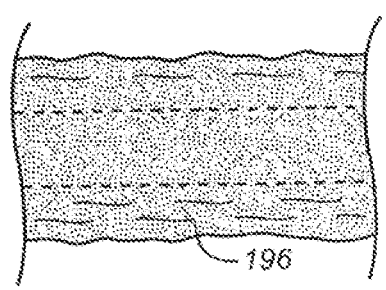 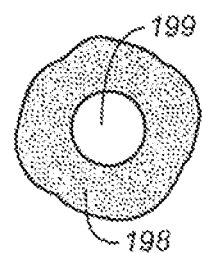
FIG. 18A  FIG. 18B  FIG. 18C
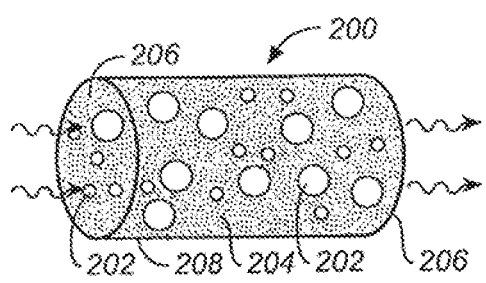 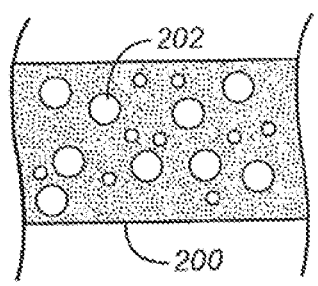 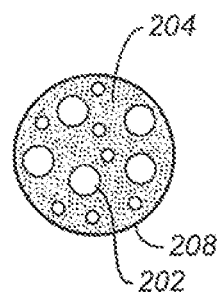
FIG. 19A  FIG. 19B  FIG. 19C

DEVICE AND METHODS FOR TREATING PARANASAL SINUS CONDITIONS

RELATED APPLICATIONS

This application is a continuation of U.S. application Ser. No. 12/883,087, filed on Sep. 15, 2010, now issued as U.S. Pat. No. 9,585,681, which is a continuation of U.S. application Ser. No. 11/398,342, filed on Apr. 4, 2006, now issued as U.S. Pat. No. 8,025,635, which claims priority to U.S. Provisional Application Ser. No. 60/668,569, filed on Apr. 4, 2005. Each of the foregoing disclosures is hereby incorporated by reference in its entirety.

FIELD

The devices, systems, and methods described here are in the field of local drug delivery to treat paranasal sinus conditions. More specifically, the treatment of paranasal sinus inflammation and rhinosinusitis is described.

BACKGROUND

Rhinosinusitis is a common paranasal sinus condition that is generally understood as encompassing sinusitis and/or rhinitis. Typically, rhinosinusitis is characterized by such major symptoms such as nasal discharge, nasal obstruction, facial congestion, facial pain/pressure, loss of smell, and fever, and such minor symptoms as headache, ear pain/pressure, halitosis, dental pain, cough, and fatigue.

The paranasal sinuses are air-filled cavities within the facial skeleton. Each paranasal sinus is contiguous with a nasal cavity and opens into the nasal cavity through a sinus ostium. The key to normal sinus function is its mucociliary transport system which is comprised of epithelial goblet cells and submucosal seromucous glands that produce nearly a quart of mucus in the sinus a day, and a ciliated, pseudostratified, columnar epithelium that lines the sinuses and which moves the mucous toward the natural sinus ostia. Any alteration in sinus ostia patency, ciliary function, or the quality of mucous may disrupt the system and lead to rhinosinusitis.

One important factor in the pathogenesis of rhinosinusitis is the patency of the sinus ostia. Partial obstruction of the sinus ostia often results in stagnation of mucous secretions, and a decrease in pH and oxygen tension within the sinus. These physiologic changes are thought to create a favorable environment for microbial infection. The microbial infection subsequently causes or enhances mucosal inflammation that may further reduce ostial patency or completely obstruct the ostia.

The medical treatment for rhinosinusitis typically includes a combination of oral antibiotics, topical or oral decongestants, steroid nasal sprays, or oral steroids such as prednisone. When medical therapy fails, which is often the case with rhinosinusitis, sinus surgery is an alternative. The most common surgery performed today is functional endoscopic sinus surgery (FESS). The goal of FESS is to improve the drainage of the sinuses by enlarging the ostia of the maxillary and frontal sinuses, and opening the ethmoid sinus area by removing the ethmoid air cells under direct visualization. However, FESS itself creates inflammation, which can lead to post-operative fibrosis, stenosis, and/or polyposis that frequently obstructs the newly opened sinuses, requiring the surgeon to reoperate to revise the ostia and insert stenting devices to keep sinus ostia patent.

U.S. Pat. No. 5,246,455 (Shikani) and U.S. Pat. No. 5,693,065 (Rains) describe stents for insertion into sinus ostia and/or sinus antrostomies or fenestrations to improve sinus drainage, reduce the degree of adhesion formation, and prevent ostial stenosis. Furthermore, stents such as the Parrell Frontal Sinus T-Stent (Medtronic Xomed, Inc., Jacksonville, Fla.), the Jasin Frontal Sinus Ostent™ Stent (Medtronic Xomed, Inc., Jacksonville, Fla.), and the Salman FES Stent (Boston Medical Products, Westborough, Mass.) are currently used after endoscopic sinus surgery for the same purpose. However, these stents are nonbiodegradable and thus require a follow-up procedure for removal. Furthermore, because these stents do not deliver a therapeutically active agent to the sinuses, they often only delay stenosis due to postoperative inflammation and the normal wound healing process. Thus, they are typically used in combination with systemic oral corticosteroids, which may result in undesirable side-effects the longer they are administered.

Sinus stents that elute drug have been proposed by others. For example, a nonbiodegradable or biodegradable polymeric "spacer" device for placement into surgically created frontal sinus fenestrations is described in U.S. Published Application No. U.S. 2004/0116958 to Goferich et al. The spacer is tubular or shaped like an hour-glass, and capable of releasing medicinal substances such as glucocorticosteroids, tyrosine kinase inhibitors, and mitosis inhibitors around newly created fenestrations. An hour-glass or tubular shape is described as preferred because it allows secretions to drain from the sinus. The spacer is placed solely at the sinus ostium and does not undergo a structural change, for example, to transition between a collapsed and expanded configuration, upon delivery to the sinus ostium. Furthermore, the spacer primarily lies within the natural ostium or surgically created fenestration. It does not have a portion that extends into the sinus cavity to contact the sinus cavity wall.

Another implantable device for treating sinusitis is described in U.S. Publication No. 2005/0245906 to Makower et al. This application describes a biodegradable polymeric device having a spacer for positioning within a sinus ostium, and a body comprised of a plurality of substance-eluting struts. The struts are configured to lie substantially parallel to the flow of mucus along the sinus cavity walls without substantially touching the walls so that mucociliary transport is not interrupted. It is uncertain how a device of this design would be constructed or deployed. Furthermore, given that the sinus mucosa is a source of water needed for device degradation and drug release, it is questionable whether this device is capable of providing a dosing regimen effective for treating rhinosinusitis because it does not substantially contact the walls of the sinus cavity.

Other compositions for the treatment of rhinosinusitis, such as aqueous solutions, creams, or gels, for topical application in the nose have also been formulated, but usually never travel far enough into the nose to reach the sinuses, are blocked from entering the sinuses due to obstructed ostia, or have such short contact with the sinus mucosa that absorption of the agent is low. For similar reasons, nasally inhaled steroid and anti-infective aerosols that have been developed to treat sinusitis are equally ineffective.

Another method that has been described for locally treating sinusitis is to place a biodegradable implant into the sinus. For example, the delivery of ampicillin from a rolled-up 1.5 cm×1.5 cm poly(lactic-co-glycolic)acid (PLGA) film to increase residence time of the antibiotic in rabbit sinuses has been investigated for the treatment of sinusitis (Min et al. Mucociliary Activity and Histopathology of Sinus Mucosa in Experimental Maxillary Sinusitis: A Comparison of Systemic Administration of Antibiotic and Antibiotic Delivery by Polylactic Acid Polymer. *Laryngoscope* 105: 835-342 (1995) and Min et al. Application of Polylactic Acid Polymer in the Treatment of Acute Maxillary Sinusitis in Rabbits. *Acta Otolaryngol* 115:548-552 (1995)). Although clinical signs of sinusitis improved over 28 days, the procedure for placing the film was quite invasive, requiring that a hole be drilled through the anterior wall of the maxillary sinus.

A less invasive method of placing a biodegradable implant into a sinus for the local treatment of sinusitis is described in commonly owned U.S. Publication No. 2005/0043706. In this application, the implant is generally delivered into the sinus through a sinus ostium, and has at least one characteristic that substantially prevents its clearance by the mucociliary transport system. For example, the implant is typically formed to possess a mucoadhesiveness that substantially prevents implant clearance from the sinus. A mucoadhesive polymer is incorporated into the implant to make it mucoadhesive. Mucoadhesive polymers are usually hydrophilic, and upon moistening, absorb water to swell and become adhesive. This implant lacks a structural component that physically maintains patency of the sinus ostium.

Consequently, new devices for locally administering active agents to the paranasal sinuses for treating paranasal sinus conditions, e.g., sinus inflammation (including, but not limited to, rhinosinusitis and sinus procedures, e.g., FESS), and for maintaining patency of sinus ostia, as well as methods for delivering the devices to the sinus cavity are desirable.

SUMMARY

The devices, systems, and methods of this invention are generally used to treat patients having a paranasal sinus condition. The paranasal sinus condition to be treated is typically postoperative paranasal sinus inflammation due to functional endoscopic sinus surgery (FESS) for sinusitis, but also includes conditions such as, but not limited to, acute sinusitis, chronic sinusitis, allergic rhinitis, rhinosinusitis, sinusitis that recurs after FESS, upper respiratory tract infections, otitis media, bronchitis, bronchiolitis, asthma, tonsillitis and other chronic diseases of the tonsils and adenoids, laryngitis, tracheitis, nasal and sinus polyposis, neoplasms of the large and small airways, and nasal, sinus, or nasopharynx tumors such as nasopharyngeal carcinoma, plasmacytomas, inverted papillomas, rhabdomyosarcomas, squamous cell carcinomas, and lymphomas, when they involve the sinuses or nasal passage. As used herein, the terms "paranasal sinus inflammation" or "sinus inflammation" refer to any reaction of sinus tissue, sinus ostial tissue, or tissue in the nasal passage proximate the sinus ostia that involves the inflammatory response. The inflammation may be caused by processes such as allergy (hypersensitivity), injury to sinus mucosa due to, e.g., trauma; surgery; infection by bacteria, viruses, fungi, chemicals, or drugs; and benign or malignant tumors.

The devices are formed in such a way to locally deliver one or more active agents into the sinus cavity, sinus ostium, and/or nasal passage for at least about one week to treat the paranasal sinus condition. The described devices are useful in surgical, non-surgical, and other therapeutic interventions related to the paranasal sinuses and nasal passages to restore anatomical function and treat any of the aforementioned conditions. Accordingly, the devices may be used to support sinus and nasal surgery, reduce the need for surgical revision, and/or prevent, delay, or reduce recurrence of rhinosinusitis.

The devices for treating paranasal sinus conditions may include a cavity member that has a first collapsed configuration that permits the device to pass through a sinus ostium and a second expanded configuration after placement into the sinus cavity. As used herein, the terms "expand", "expansion", or "expanding", refer to a device that undergoes physical expansion, e.g., from a compressed to an expanded state, not expansion due to the absorption of water.

In their expanded configuration, the devices in some variations have a surface area to volume ratio that is substantially unchanged from that of the devices in their collapsed configuration. In other variations, upon expansion, the cavity member also at least partially conforms to the shape of the sinus cavity and substantially contacts the mucosa of the sinus cavity. The devices may be made from any biocompatible material. For example, they may be formed from various metals and their alloys, biodegradable or nonbiodegradable polymers, and combinations thereof.

In addition to a cavity member, the devices may include a nasal portion and an ostial member that is configured to reside within the sinus ostium. The cavity member is attached to the distal end of the ostial member. The nasal portion is attached to the proximal end of the ostial member and lies within the nasal passage. The active agent may be incorporated into all portions of the device or only included in the expandable cavity member, the ostial member, or nasal portion. In one aspect, the active agent is released from the cavity member and the ostial member. In another aspect, the active agent is released from the cavity member and nasal portion. In yet a further aspect, the active agent is released from the nasal portion and the ostial member. The cavity member, ostial member, and nasal portion may contain and deliver the same or different active agents.

The paranasal sinus devices may deliver an active agent(s) over at least about one week, over at least about two weeks, over at least about three weeks, over at least about one month, over at least about two months, over at least about three months, over at least about four months, over at least about five months, or over at least about six months or more. Typically, the active agent is delivered over about four weeks.

The devices may be formed from one or more polymeric pliable filaments. For example, the filaments may be configured to form cavity members that resemble a fringed structure, a flexible mesh, a whisk-like structure, and the like. The cavity members may be formed to be expandable. In one variation, the cavity members self-expand. In another variation, the devices expand after application of an expansive or mechanical force. For example, the devices may expand after balloon inflation. In some instances, the cavity members expand to substantially contact the sinus cavity wall after deployment within the sinus. Contact with the sinus cavity wall may be verified by incorporation of radiopaque markers on or within the cavity members, or visualization using endoscopy or other imaging modalities.

In another variation, the pliable filament(s) may contain a plasticizer or a solvent which softens the biodegradable or nonbiodegradable polymer. Balloon inflation or other mechanical types of expansion may be used to expand variations of the plasticized cavity member that are not configured to self-expand. Upon contact of the plasticized cavity member to the mucosal tissue, the plasticizer diffuses out of the cavity member. The plasticizer diffusion hardens the cavity member in such a way that the cavity member substantially conforms to the shape of the sinus cavity. As an example, a filament made from lactide/glycolide polymer may be plasticized with materials such as triethyl citrate, acetone and other ketones, ethanol and other alcohols, N-methyl pyrrolidone, ethyl acetate and mixtures thereof. Upon placement of the filament into the sinus, the plasticizer, triethyl citrate, for example, diffuses out of the filament polymer to result in a hardened filament that substantially conforms to the shape of the sinus cavity.

The devices described here for treating a paranasal sinus condition may include an active agent dispersed within a biodegradable polymer matrix, in which the device comprises a cavity member, an ostial member, and optionally a nasal portion, and exhibits an in vivo cumulative release profile in which a therapeutically effective amount of said active agent is maintained in a sinus tissue for at least about 4 days, at least about 14 days, at least about 25 days, or at least about 35 days after implantation of the device.

The paranasal sinus devices may be delivered into a sinus using inserters of various designs. Typical inserters include a conduit, e.g., a catheter, needle, or angiocatheter, having a lumen. For example, the conduit may be made such that it has variable stiffness along its length. In addition, the distal portion of the conduit may be pre-angulated to facilitate access of the sinus ostium, or made such that the distal portion is malleable such that the physician may angulate the conduit prior to accessing the sinus ostium.

The paranasal sinus devices and inserters for their deployment may be used in a system for treating a paranasal sinus condition. In general, the system works by first placing the inserter having one or more devices in a collapsed, folded, or constrained configuration within or carried on its distal end through the sinus ostium. Once within the sinus, the cavity member of the device transitions from the first collapsed, folded, or constrained configuration to a second expanded configuration. For example, a sheath may be retracted to slidably deploy a self-expanding cavity member that contacts a substantial portion of the sinus cavity wall. Balloon inflation or other mechanical types of expansion may be used to expand variations of the cavity member that are not configured to self-expand.

DESCRIPTION OF THE DRAWINGS

FIGS. 8A-8C show perspective, ostial, and end views of a coil-like ostial member.

FIGS. 9A-9C show perspective, ostial, and end views of a accordion-like ostial member.

FIGS. 10A-10C show perspective, ostial, and end views of a mesh-like ostial member.

FIGS. 11A-11C depict perspective, ostial, and end views of a star-like ostial member.

FIGS. 12A-12C show perspective, ostial, and end views of a hexagonal shaped ostial member.

FIGS. 13A-13C depict perspective, ostial, and end views of a furled sheet-like ostial member.

FIGS. 17A-17C show perspective, ostial, and end views of an ostial member configured as an expandable pleated tube.

FIGS. 18A-18C show perspective, ostial, and end views of an ostial member made from gel foam.

FIGS. 19A-19C show perspective, ostial, and end views of a cylindrical ostial member having a plurality of lumens.

DETAILED DESCRIPTION

The paranasal sinus devices of this invention may take various forms. For example, some are designed to include a cavity member, an ostial member, and a nasal portion, and deliver active agents for the treatment of paranasal sinus conditions, e.g., sinus inflammation. The cavity member may have a first collapsed configuration that permits it to be inserted through a sinus ostium or surgically created fenestration, and a second expanded configuration upon placement into the sinus cavity. In this variation, once expanded, the structure of the cavity member generally has a surface area to volume ratio that is not substantially different from the surface area to volume ratio of the cavity member in its collapsed configuration. This may be important because the sinus mucosa is a source of water needed for the release of the active agent from the paranasal sinus device. Thus, if the surface area of a device available for contacting the sinus mucosa is decreased, e.g., in relation to its volume, dissolution (and subsequent absorption) of the active agent should also be decreased. Furthermore, once expanded, the cavity member may also substantially contact the sinus cavity wall.

The nasal portion generally functions to position and/or anchor the device at the sinus ostium, preventing lateralization of the middle turbinate, occlusion of the middle meatus, and formation of tissue adhesions. The ostial member located at the proximal end of the cavity member typically functions to maintain patency of the sinus ostium. However, as further described below, each component of the device may have various functions, depending on factors such as the particular structure of the cavity member, ostial member, or nasal portion and whether the component is capable of releasing an active agent.

Figure 1:
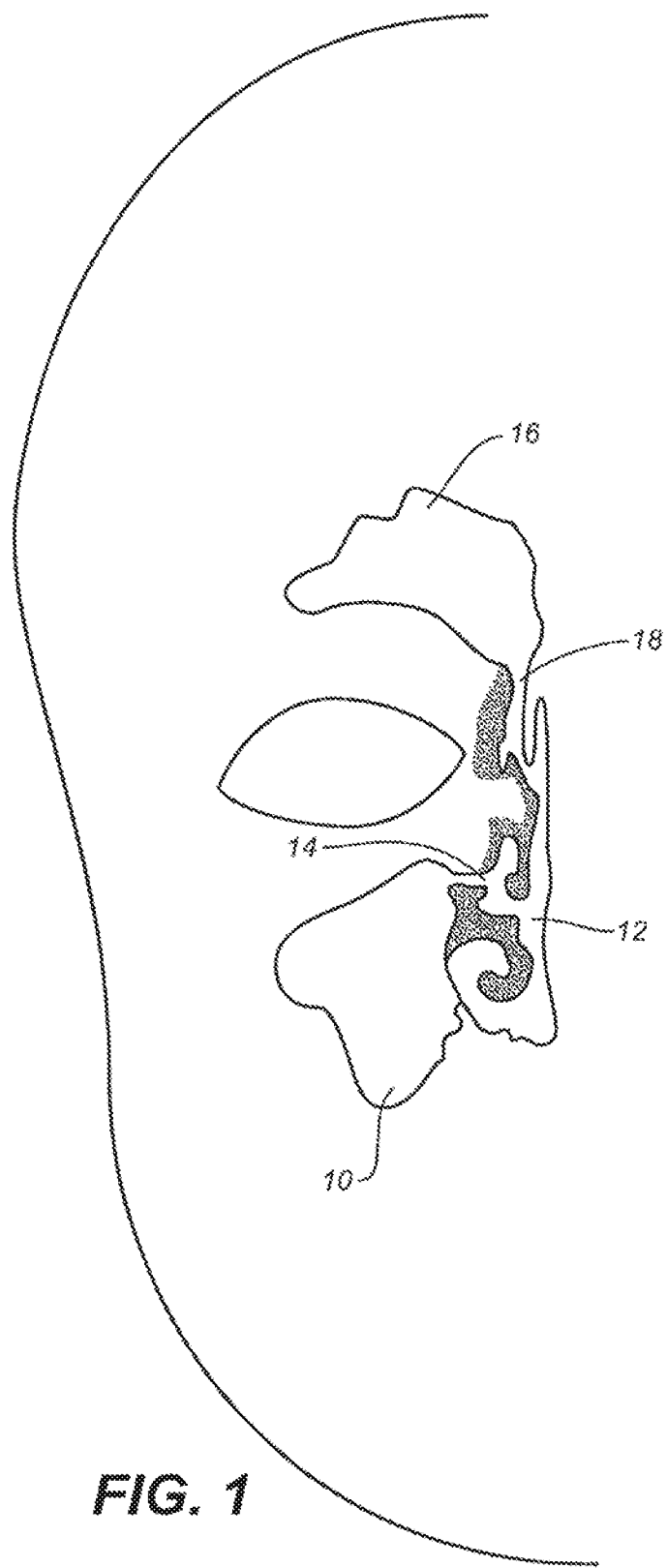
FIG. 1 is a cross-sectional view of a maxillary and frontal sinus.
Figure 2A:
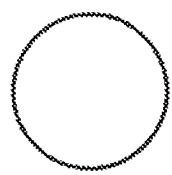
FIGS. 2A-2M are transverse cross-sectional views of various pliable filaments.
Figure 2B:
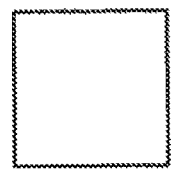
Figure 2C:
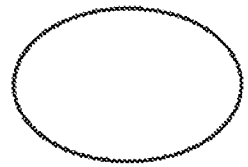
Figure 2D:
Figure 2E:
Figure 2F:
Figure 2G:
Figure 2H:
Figure 2I:
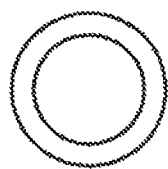
Figure 2J:
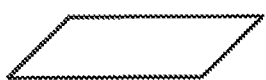
Figure 2K:
Figure 2L:
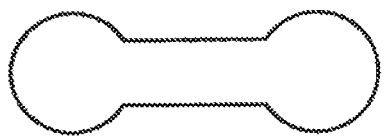
Figure 2M:

As used herein, the terms "paranasal sinus" and "sinus" are used interchangeably, and refer to all sinuses, i.e., the maxillary, frontal, ethmoid, and sphenoidal sinuses. Each sinus cavity opens into the nasal cavity through a sinus ostium. As shown in FIG. 1, the maxillary sinus 10 opens into nasal cavity 12 at maxillary sinus ostium 14, and the frontal sinus 16 opens into nasal cavity 12 at frontal sinus ostium 18. As used herein, the terms "treat", "treating", or "treatment" refer to the resolution, reduction, or prevention of a paranasal sinus condition or its symptoms, prevention of complications attributable to a paranasal sinus condition, or provision of a beneficial substance, to a paranasal sinus. For example, the beneficial substance may be used to promote general health of the sinus.

Once expanded, the cavity member may be configured to conform at least partly to the shape of the sinus cavity and substantially contact the sinus cavity wall. By "substantially contact" it is meant the percentage of surface area of the cavity member generally required to contact a sinus cavity wall (sinus mucosa) that provides the appropriate release kinetics for the active agents throughout a treatment period, for example, for at least one week, for at least two weeks, for at least three weeks, or for at least four weeks or more. Accordingly, depending on the amount of surface area needed for contact, "substantial contact" may refer to contact of about 10% to about 100%, about 20% to about 100%, about 30% to about 100%, about 40% to about 100%, about 50% to about 100%, about 60% to about 100%, about 70% to about 100%, about 80% to about 100%, or about 90% to about 100% of the surface area of the device to the sinus cavity wall. Importantly, the pressure of the cavity member on the sinus mucosa is sufficient for maintaining contact of the cavity member against the sinus mucosa but does not cause significant damage or necrosis to the mucosa.

As used herein, the terms "active agent", "therapeutic agent", and "drug" are used interchangeably and refer to any substance used to treat a paranasal sinus condition. Furthermore, as used herein, the term "therapeutic amount" refers to a concentration of active agent that has been locally delivered to a sinus or nasal passage that is appropriate to safely treat a paranasal sinus condition.

General Elements.

The paranasal sinus devices described here may be configured in a variety of ways. For example, they may be formed from one or more filaments, which include any linear structure such as strands, capillaries and tubular and non-tubular structures, but may also be formed from a film or sheet-like starting material. The filaments may be of variable stiffness and take a variety of suitable forms, such as threads, ribbons, strips, beaded structures, tubes, and the like, so long as they are flexible enough to substantially contact a portion of a sinus cavity wall after deployment, exhibit the desired release kinetics, and deliver an amount of drug therapeutic for a paranasal sinus condition. The filaments may be of different shapes generally, and have a variety of cross-sectional shapes, as desired or as useful to maintain mucosal contact and consistent deployment. For example, as shown in FIGS. 2A-2M, they may be shaped to be circular (2A), square (2B), elliptical (2C), winged (2D), diamond-like (2E), rectangular (2F), wedged (2G), ramped (2H), tubular (2I), parallelogram-like (2J), arc-like (2K), dog bone/dumbbell shaped (2L), slightly concave (2M), and the like on transverse cross-section. If desired, the pliable filaments may also be combined to form woven structures such as cords, ropes, braids, mesh, and the like. Tubular filaments may be combined into structures with multiple lumens, in either concentric or adjacent configurations, or directly formed as filaments with multiple lumens. Films and sheets may also include non-woven meshes and largely two dimensional materials, where dimensional thickness is much less than dimensional length or width. Other materials such as gelfoam may form such filaments upon their application.

Figure 6A:
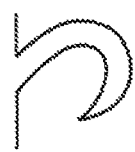
FIGS. 6A-6F are side cross-sectional view of various filament anchoring mechanisms.
Figure 6B:
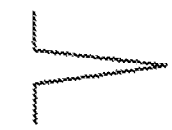
Figure 6C:
Figure 6D:
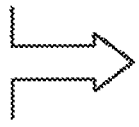
Figure 6E:
Figure 6F:

In some variations the pliable filaments may be configured to include one or more anchoring elements to help affix the filaments to the sinus mucosa or otherwise enhance contact of the filaments to the sinus mucosa. For example, as shown in FIGS. 6A-6F, the anchoring element may be one or more hooks (6A), spikes (6B), opposed spikes (6C), arrows (6D), ridges (6E), barbs (6F), and the like. In FIG. 6E, ridges may also be formed to be triangular, square, round, semicircular, and the like.

Cavity Member.

The cavity members are generally biodegradable, but they may also be made to be nonbiodegradable. Additionally, whether formed as biodegradable or nonbiodegradable, the cavity members may be attached to a component, for example, a wire or suture, that extends from the cavity member and out through the ostium, which could be grasped by an instrument to remove it from the sinus.

Figure 3A:
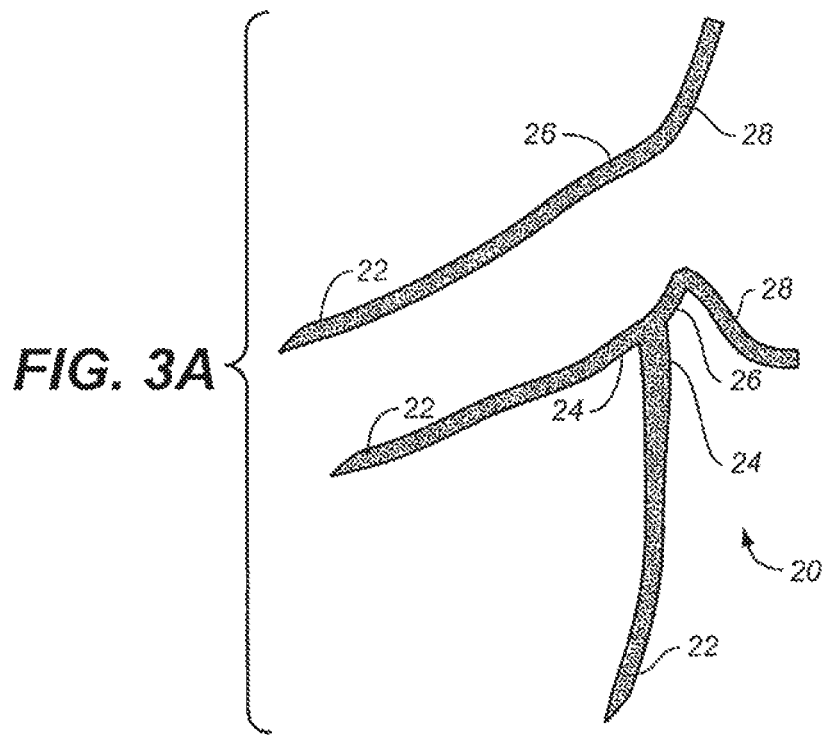
FIG. 3A is a cross-sectional view of a maxillary sinus device having a fringed structure according to one variation of the invention.
Figure 3B:
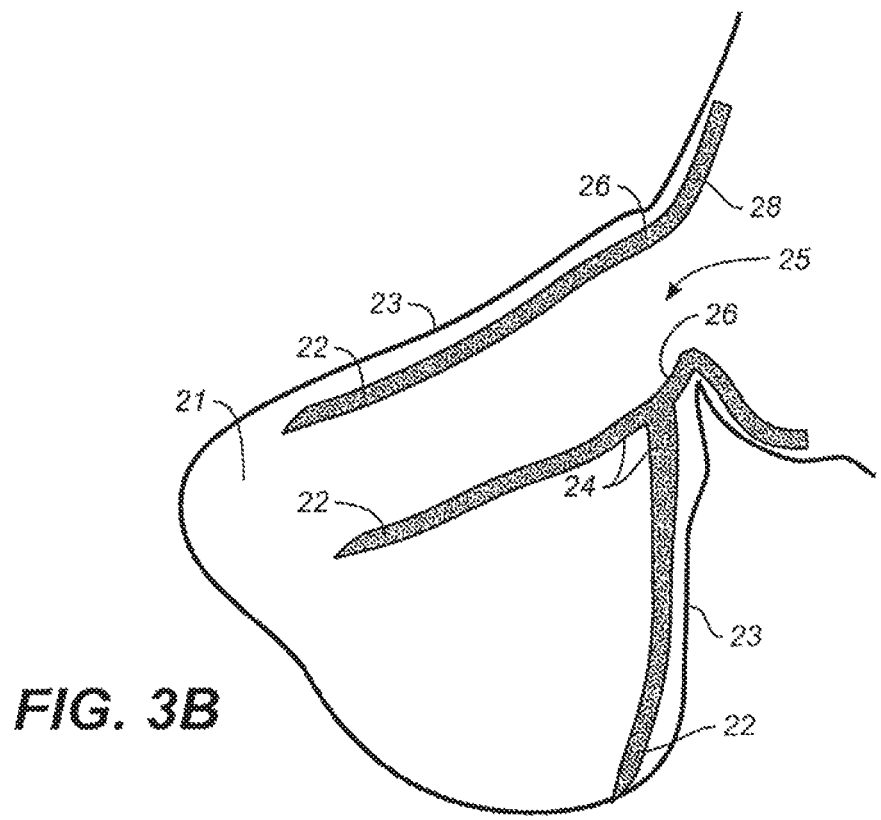
FIG. 3B is a cross-sectional view of the paranasal sinus device of FIG. 3A in a maxillary sinus.

In one variation, the pliable filaments are configured to form a fringed structure. As shown in FIG. 3A, a cross-section of fringed structure 20 includes a plurality of pliable filaments or prongs 22 (expanded configuration). Pliable filaments 22 are secured at their proximal ends 24 to a tubular ostial member 26. Once deployed in a paranasal sinus such as maxillary sinus 21 in FIG. 3B, pliable filaments 22 radially expand, unfurl, or otherwise are adapted to undergo a change in configuration after insertion into a sinus, to substantially contact the sinus cavity wall 23 and to deliver an active agent into the sinus 21. The length of the pliable filaments 22 is usually between about 1 cm and about 6 cm, more usually between about 2 cm to about 6 cm, and more usually still between about 3 cm and 6 cm. In addition, ostial member 26 is placed at the sinus ostium 25 to maintain ostium patency so that drainage from the sinus 21 to the nasal cavity is uninterrupted. Nasal portion 28 may also be provided on the proximal end of the device. Nasal portion 28 extends into the nasal cavity and may minimize lateralization of the middle turbinate to the lateral nasal wall and ostia opening, further reducing the possible risk of occlusion and adhesion formation in the middle meatus.

Figure 4A:
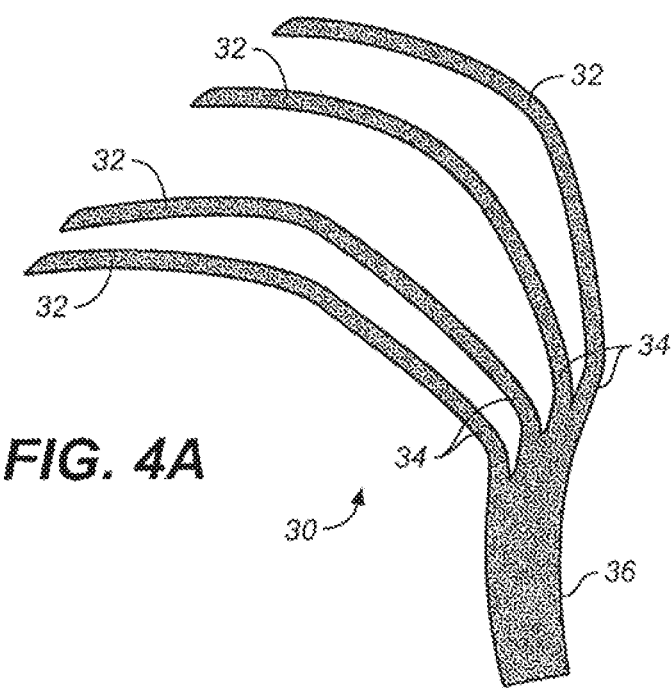
FIG. 4A is a cross-sectional view of a frontal sinus device having a fringed structure according to another variation of the invention.
Figure 4B:
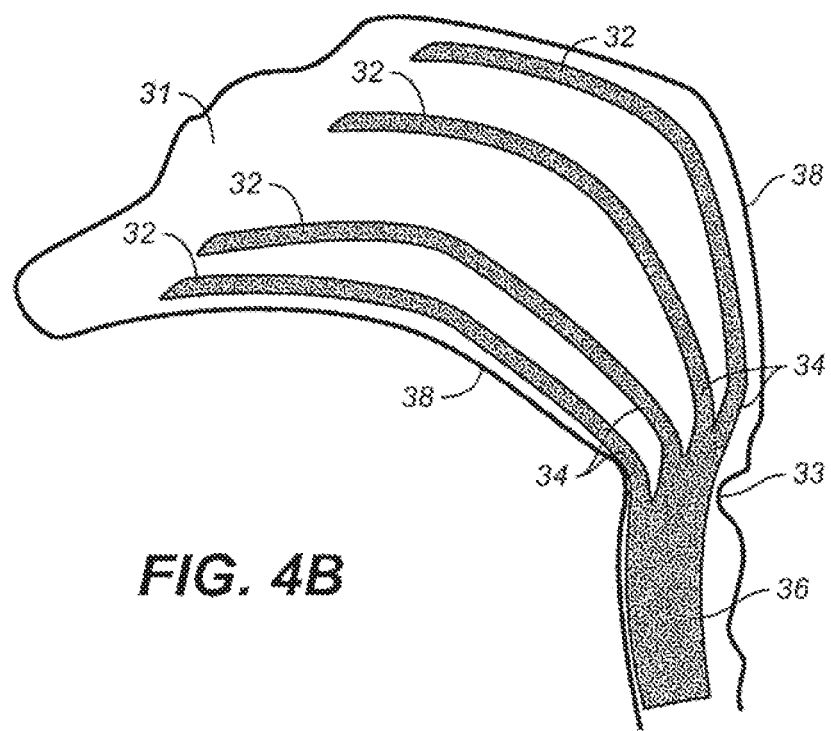
FIG. 4B is a cross-sectional view of the paranasal sinus device of FIG. 4A in a frontal sinus.

In another variation, shown in FIGS. 4A and 4B, pliable filaments 32 are configured to form a fringed structure 30 in a frontal sinus 31. Like in FIGS. 3A and 3B, pliable filaments 32 are secured to ostial member 36 at their proximal ends 34, and once deployed, substantially contact the sinus cavity wall 38 to deliver drug into frontal sinus 31. The length of pliable filaments 32 are usually between about 1 cm and about 5 cm, and more usually between about 2 cm and about 5 cm. However, because of the longer passageway from the nasal cavity to the frontal sinus ostium 33 than to the maxillary ostium, and because the frontal sinus device 30 is subject to gravitational pull, as well as encompasses a longer narrower cavity prone to stenosis, adhesions and scarring, the tubular ostial member 36 is generally formed to be longer in a frontal sinus device. However, the length of ostial member 36 may be shortened if the fringed structure 30 (or other cavity member) is configured to anchor the device within the sinus cavity, or if the risk of such aforementioned complications has been reduced through varying surgical techniques (more or less extensive) or anatomical variations.

Figure 5A:
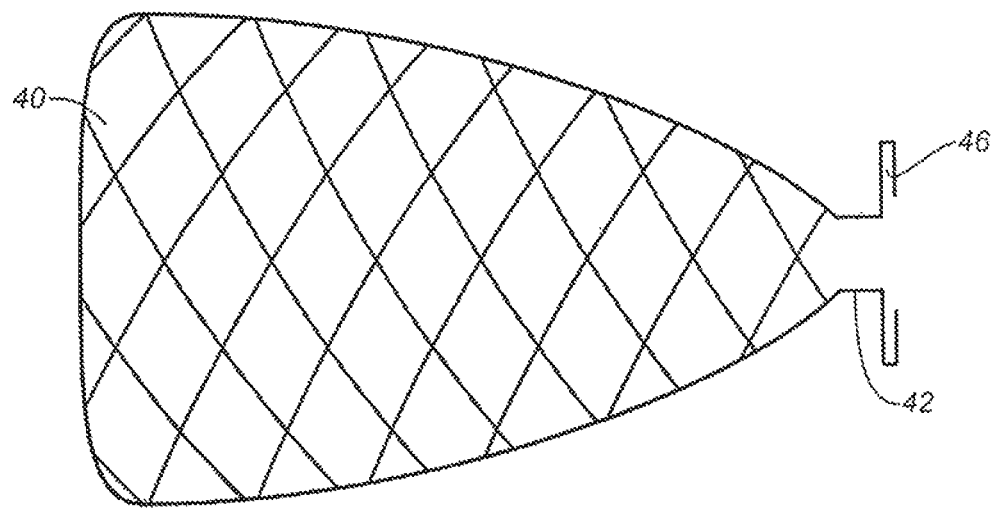
FIG. 5A is a side view of a paranasal sinus device including an expandable mesh according to another variation of the invention.
Figure 5B:
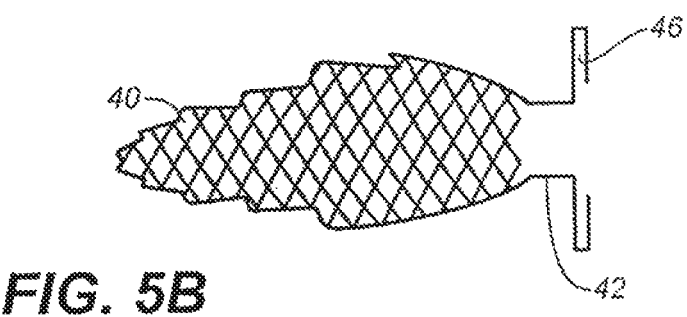
FIG. 5B is a side view of the paranasal sinus device of FIG. 5A prior to expansion.

Turning to the variation shown in FIGS. 5A and 5B, the pliable filaments are configured to form a flexible mesh. In FIG. 5B (collapsed configuration), flexible mesh 40 is secured to an ostial member 42 (and in some instances, also to nasal portion 46) by methods well known in the art, e.g., by welding, annealing, heat bonding, attachment bands or adhesives such as thermoplastic adhesives, thermosetting adhesives, rubber-resin blend adhesives, and other adhesives well known in the art. Upon expansion, as shown in FIG. 5A, flexible mesh 40 forms a spherical structure capable of at least partially conforming to the shape of a sinus cavity. The weave of the mesh may be adjusted to be looser or tighter, or the width of the pliable filaments may be adjusted to correspondingly adjust the flexibility of the mesh. The flexible mesh may be expanded to a diameter between about 1 cm to about 5 cm, and more usually between about 2 cm to about 5 cm, and as further described below, may form a self-expanding, controllably expandable, or balloon expandable cavity member.

The cavity member may be of various other designs. In one variation, the cavity member 70 is configured as a single pliable filament 72 (FIG. 7A). Single pliable filament 72 may curve in such a way to at least partially conform to the shape of the sinus of implantation and substantially contact the sinus cavity wall. In another variation, as shown in FIG. 7B, the cavity member 74 comprises a single pliable filament configured as a coil 76. The number of turns of the coil will vary depending on such factors as the sinus of implantation, placement and deployment technique used, and whether or not the coil is to be used as an anchor or for drug delivery, and flexibility of the filament. Similarly, a cavity member 78 may be made from a single pliable filament configured and/or inserted as a random coil 80 (FIG. 7C).

Figure 21:
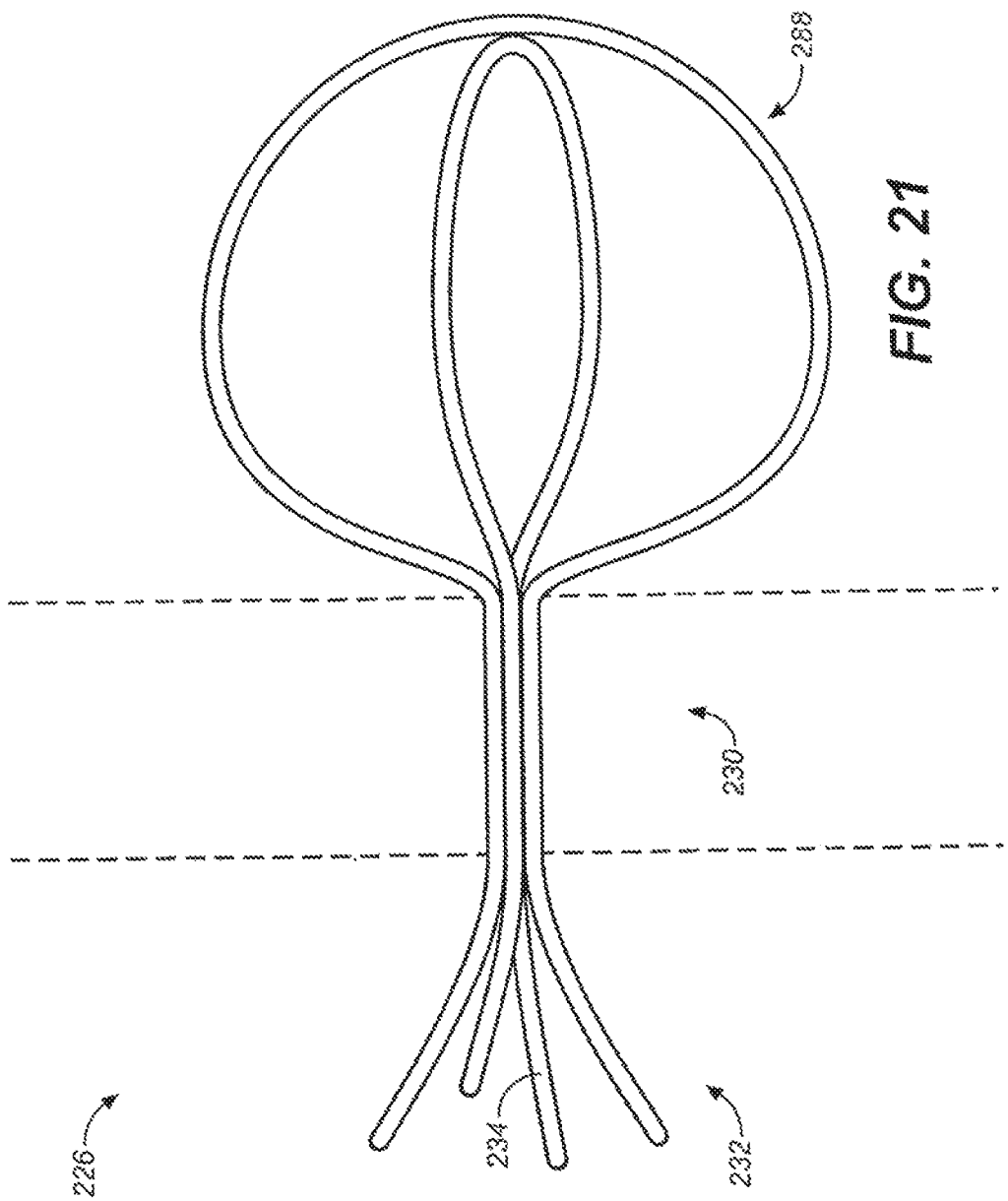
FIG. 21 depicts a perspective view of an exemplary paranasal sinus device.

In other variations, the cavity member is formed from a plurality of one or more arced or looped filaments. For example, in FIG. 7D, the expanded cavity member 82 is formed from two pliable filaments 84. Pliable filaments 84 are configured to form concentric loops crossing each other. The loops are usually affixed to each other by methods described above to form a distal apex 86. The proximal ends 88 of pliable filaments 84 may be joined and otherwise configured to form an ostial member 230 and/or nasal portion 232, e.g., as shown in FIG. 21. In another variation, expanded cavity member 90 is formed from a plurality of pliable filaments 92 configured to form multiple free loops (FIG. 7E). The proximal ends 94 of pliable filaments 92 may also be joined or otherwise configured to form an ostial member and/or nasal portion of the device. In yet a further variation, as shown in FIG. 7F, the expanded cavity member may be formed from a plurality of pliable filaments 98 configured as a whisk-like structure. The spacing 100 between the filaments may be varied depending on the particular desired cavity member configuration. The filaments may be shaped by adjusting their degree of flexibility, e.g., by addition of plasticizer, use of various molding, casting, bonding, and extrusion techniques, and by other methods well known in the art. The angle between each looped filament may also be varied depending on the particular desired cavity member configuration. Any number of filaments may also be employed to fabricate devices with any number of arced or looped cavity members.

Figure 7I:
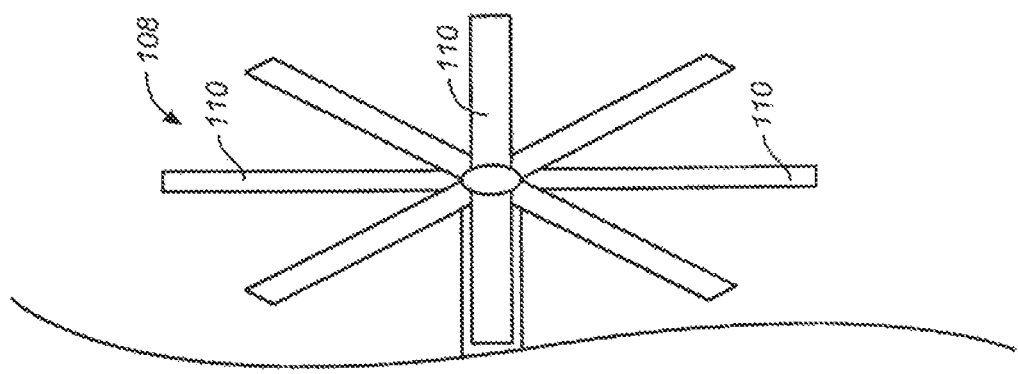
FIGS. 7A-7R are perspective views of various cavity member configurations.
Figure 7H:
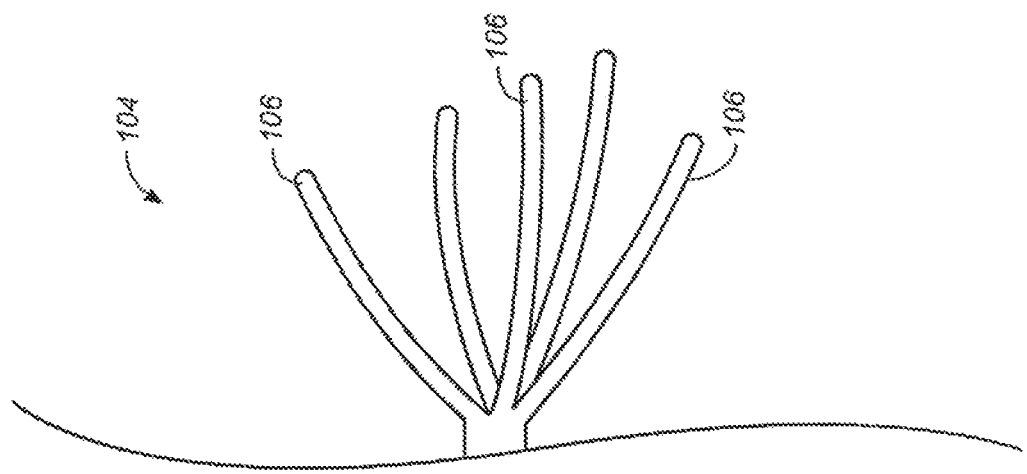
Figure 7G:
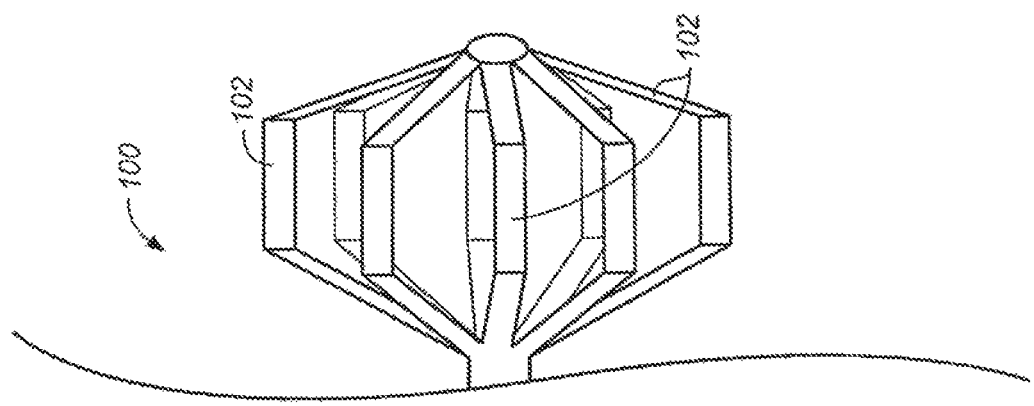
Figure 7L:
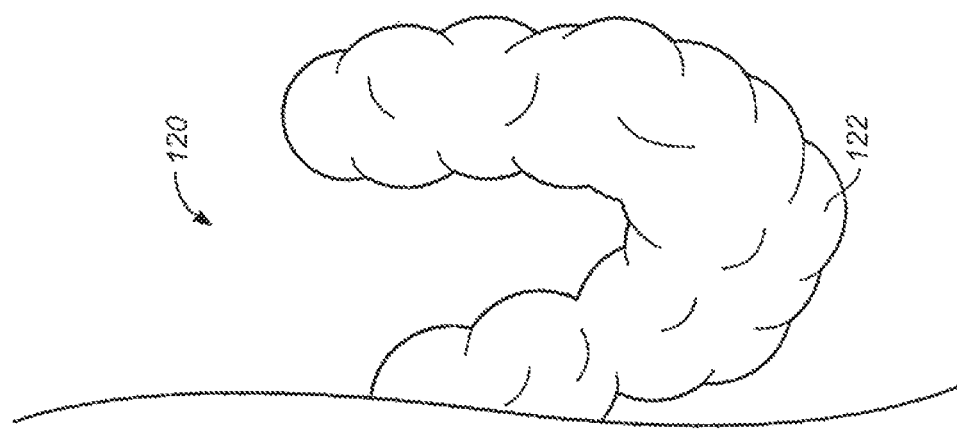

In yet other variations, the cavity members may be formed from ribbon or strip-like filaments. For example, as shown in FIG. 7G, the cavity member 100 is formed from a plurality of strip-like sub-filaments 102 resulting from slitting a single tubular filament structure. In FIG. 7H, the cavity member 104 is formed from a plurality of strip-like filaments 106 configured as a pronged structure. In FIG. 7I, the cavity member 108 is made from a plurality of strip-like filaments 110 resulting from slitting and deformation of "children" filaments from the end of a single "parent" tubular filament structure.

Figure 7K:
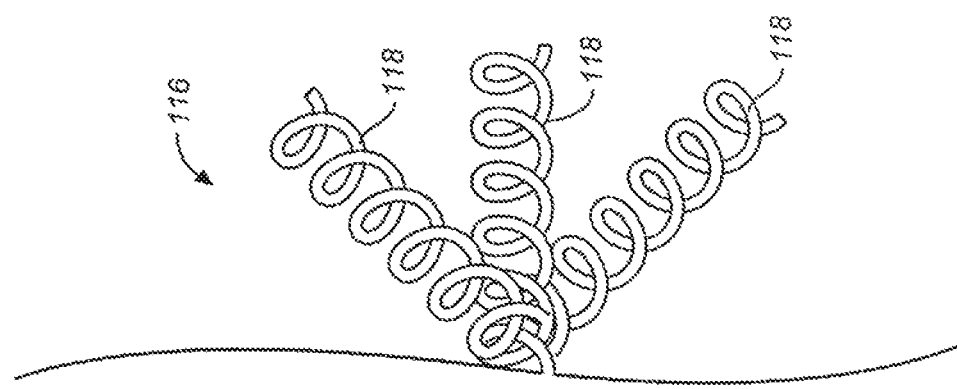
Figure 7J:
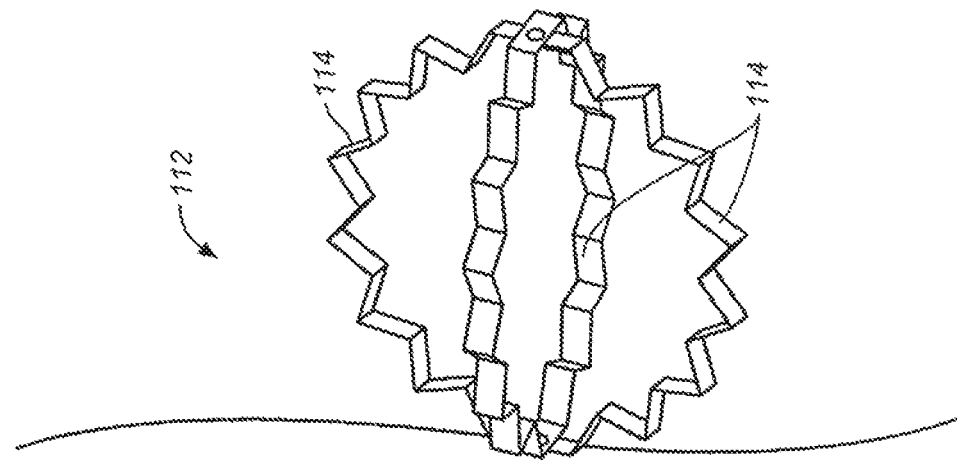
Figure 7O:
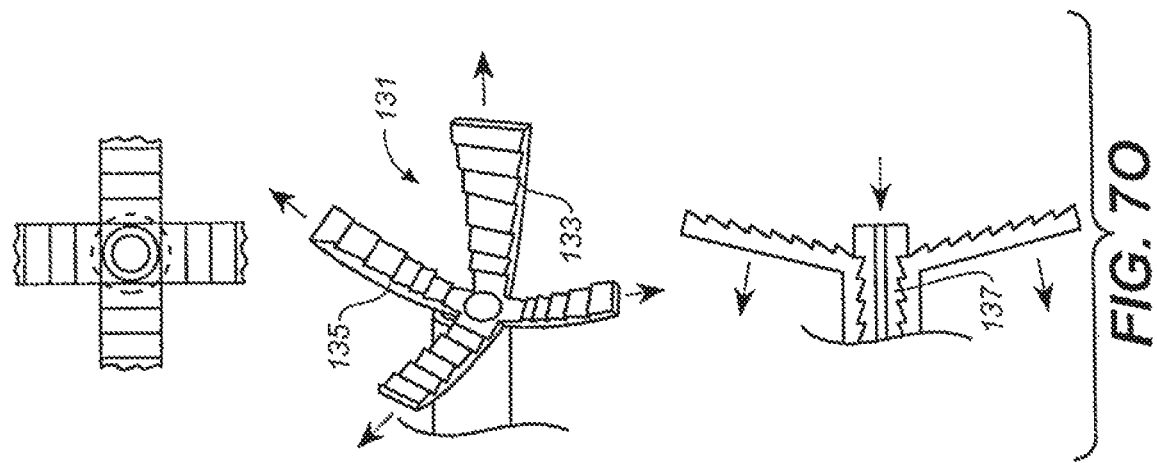
Figure 7N:
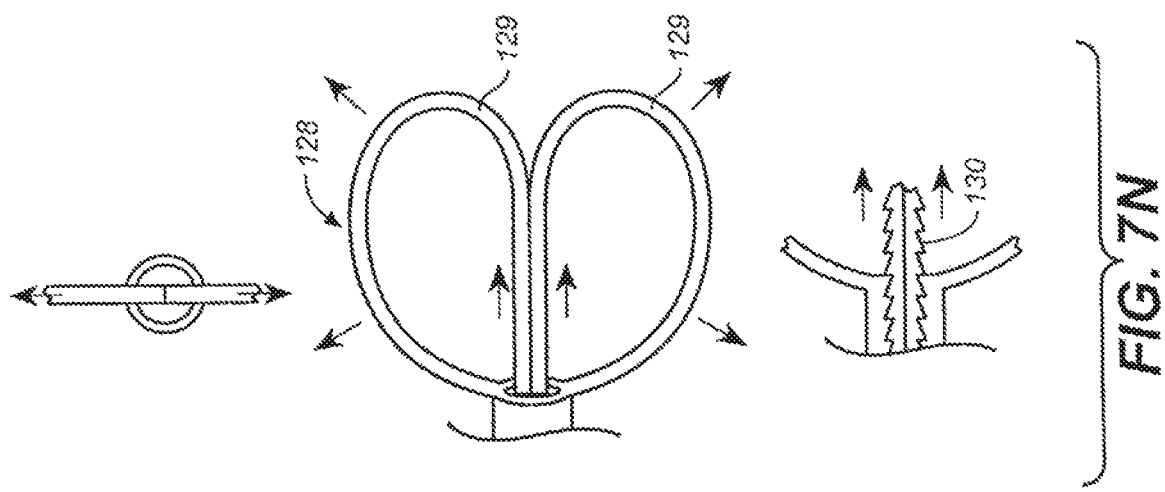
Figure 7M:
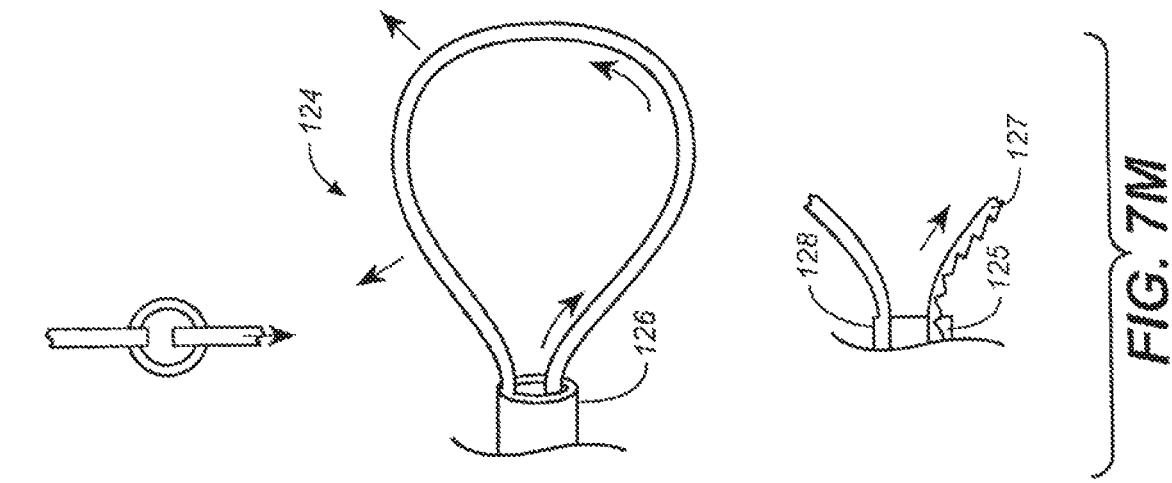

FIGS. 7J-7O show yet further cavity member design variations. In FIG. 7J, cavity member 112 is formed from a plurality of corrugated ribbon-like filaments. In FIG. 7K, cavity member 116 is formed from a plurality of filaments configured like springs 118. The cavity member may also be made from one or more filaments 122 comprising gelfoam. FIGS. 7M-7O also include features allowing the irreversible deployment of one or more filaments in an open or tensed configuration using ridges (for example 134, 136) on the filaments and opposing ridges upon the adjacent lumens or other structures at their insertion site. In FIG. 7M, a cavity member 124 consisting of a single ridged loop is inserted into the sinus and against the sinus wall (arrows) through a lumen with an opposing ridge 125 on the ostial member 126 of the device. In FIG. 7N, a cavity member 128 consisting of two opposed loops 129 is similarly inserted. These ridges 130 may alternatively deform the structure of the sinus cavity member. In FIG. 7O, a cavity member 131 of the type described in above in FIG. 7I is modified by the addition of ridges 133 on the interior of strip-like filaments 135, and an additional interior tubular member with opposing ridges 137 positioned concentrically within the parent slit tube. The device's cavity member strip-like filaments 135 are deployed through their deformation along the intersection of the strip ridges and those of the opposing interior ridges as the concentric member 137 is independently pulled back (towards the proximal direction) while maintaining constant the position of the external sinus cavity parent slit tube. The result is a splayed and deformed open pattern of slit "children" filaments along the sinus cavity wall.

Figure 7R:
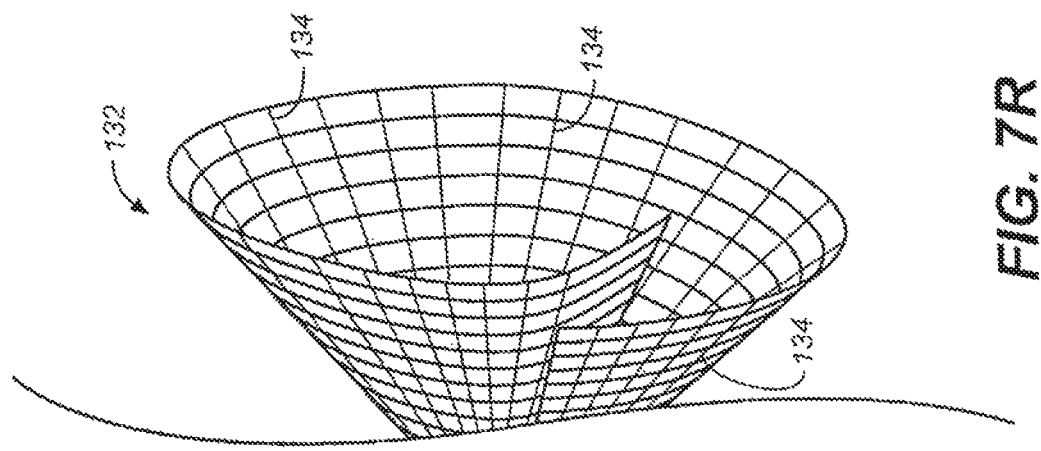
Figure 7Q:
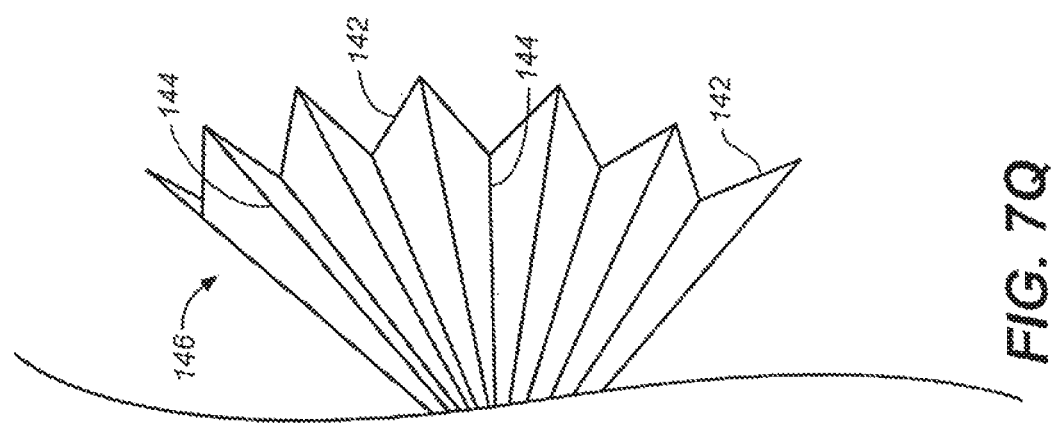
Figure 7P:
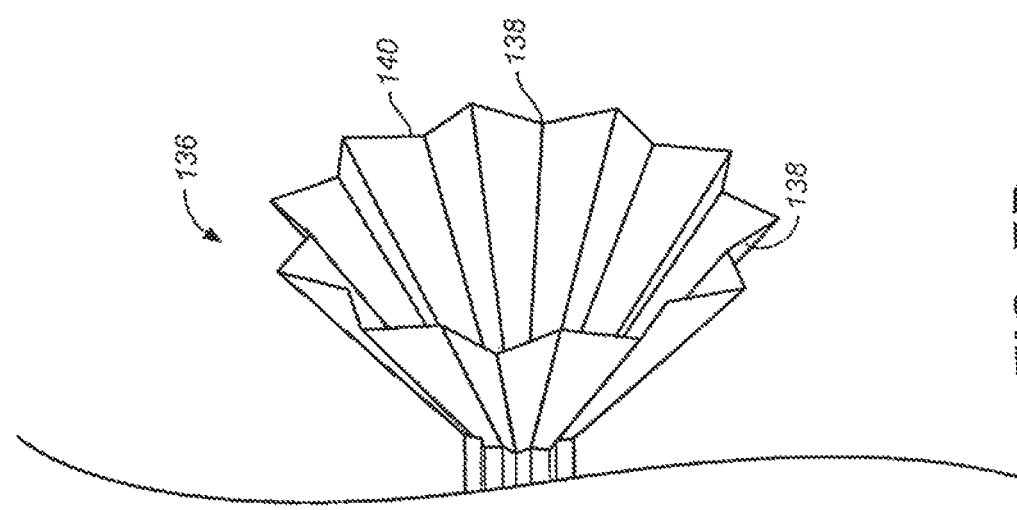
Figure 14A:
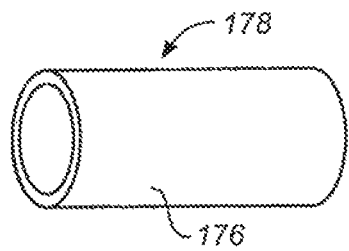
FIGS. 14A-14C depict perspective, ostial, and end views of a tubular ostial member.
Figure 14B:
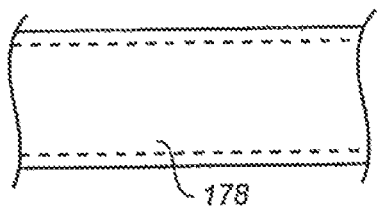
Figure 14C:
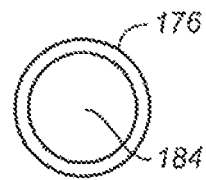

In FIG. 7R, the cavity member 132 is formed from a plurality of filaments 134 woven as a mesh and configured as a funnel-type structure. The cavity members may also be formed from a film, non-woven, or sheet-like material. For example, the film or sheet may be pleated, as shown in FIGS. 7P and 7Q. In FIG. 7P the sheet 140 has pleats 138 that allow the cavity member 136 to be configured as a pleated cone. In FIG. 7Q, the sheet 142 has pleats 144 that allow the cavity member 146 to be configured as a pleated fan.

The cavity members of the invention may be adapted to self-expand, e.g., if they are made from a shape memory polymer or if they are constrained by a sheath prior to sinus insertion and deployed in the sinus after retraction of the sheath. They may also be expanded via methods involving mechanical expansion. For example, they may be expanded by inflating a balloon or pulling a cord or wire attached to the distal end of the device, or by the application of expansive force at the proximal end of the device, or by deflecting or deforming the cavity member along the sinus walls. However, in addition to the methods previously described, the invention also contemplates mechanical expansion of cavity members made from less pliable filaments that are equipped with one or more joints or hinges and which expand by movement of the pliable filaments at the joints or hinges. The joint or hinge may be an area of greater flexibility along the filament due to use of a polymer in that area having a lower durometer, decreasing the width of the filament, or by adjusting other surface features or mass density of the filament in that area.

The active agent may be included in any portion of the device, e.g., the cavity member, ostial member, and/or nasal portion. When filaments are used, the active agent may be incorporated in the filaments as drug dispersed or dissolved within a polymeric matrix, or coated on the pliable filaments, or first encapsulated, such as microencapsulated, and then incorporated within or coated onto the pliable filaments. In some instances, the pliable filaments may be constructed to have one or more pouches or pockets for holding pellets of drug. The dosage of active agent delivered by the cavity member may be adjusted by, e.g., increasing or decreasing the number of drug-containing filaments in the cavity member, increasing or decreasing the amount of drug contained within or coated on the filaments, or by forming the pliable filaments such that they can be broken or cut into smaller filaments either before or after insertion into a sinus cavity. For example, the pliable filaments may include predetermined fracture lines or markings that a physician can use as a guide to adjust filament length prior to insertion, or after insertion into the sinus, the filaments may be adapted to preferentially degrade at the fracture lines into smaller filaments. In some instances, it may be desirable to include filaments having different active agents in the cavity member.

Cavity members may also be made from a combination of pliable filament configurations or from combinations of filaments and other described cavity member configurations. For example, the structures of FIGS. 3A-3B and FIGS. 4A-4B could be used to support the flexible mesh of FIG. 5A. If desired, a radiopaque marker may also be included on one or more pliable filaments to indicate the degree of expansion of the cavity member upon radiographic imaging. Usually, the marker will be detected by fluoroscopy, and if nonbiodegradable, will exit the sinus with the normal mucus flow if and after the expandable cavity member has degraded. Biodegradable radiopacifiers such as particles of an iodinated contrast agent or bismuth salts may also be used. Contact with the sinus cavity wall may be verified by incorporation of radiopaque markers on or within the cavity members, or visualization using endoscopy or other imaging modalities.

Contact and/or anchoring of the cavity member to the sinus cavity wall may be enhanced by the addition of mucoadhesive materials, that may or may not be polymeric, to the pliable filaments, as further described below, by adjusting filament dimensions (e.g., decreasing filament diameter or otherwise decreasing aspect ratio), or by forming the filaments, as shown in FIGS. 6A-6F, such that they include hooked (7A), spiked (7B), double spiked (7C), arrow-like (7D), ridged (7E), or barb-like structures (7F), or other anchoring or texturizing elements for grasping the sinus mucosa. In other variations, the filaments may be configured toward their distal ends as screws or springs which are capable of being fixed in sinus mucosa or other sinus tissue by insertion or tension. In yet other variations, the filaments may be fixed to the sinus cavity wall by stapling or suturing. The cavity member may also be anchored in the sinus by adjusting its size such that it is too large to move out of the ostium, or configuring the cavity member such that it expands to fill the entire sinus cavity or expands to exert sufficient pressure to maintain it within the sinus cavity. Furthermore, the paranasal sinus devices may have pliable filaments configured to have flexibility such that portions of the cavity members can differentially bow to conform to the shape of the sinus in which it is deployed.

Ostial Member.

The ostial member may be used to keep the ostia patent and/or anchor the nasal portion or cavity member of the device. In some variations, its inclusion may be to simply connect the cavity member to a nasal portion or other extra-sinus portion of the device. The ostial member is mounted to the proximal end of the cavity member, and is positioned at or relatively near the sinus ostium. Again, the pressure generated by the ostial member on the sinus mucosa is sufficient to keep the ostium open, but not so great that it compromises blood flow to the sinus mucosa.

Figure 15A:
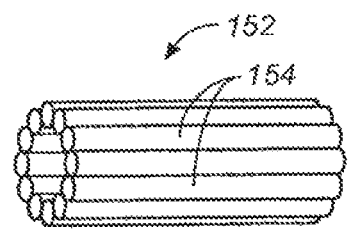
FIGS. 15A-15C show perspective, ostial, and end views of an ostial member formed from a plurality of pliable filaments.
Figure 15B:
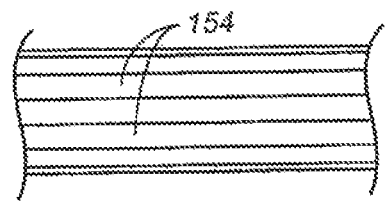
Figure 15C:
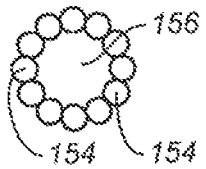
Figure 16A:
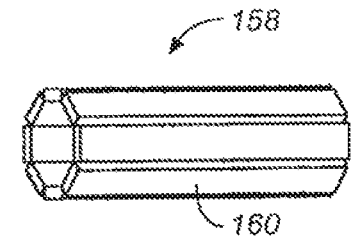
FIGS. 16A-16C depict perspective, ostial, and end views of an ostial member formed from a plurality of pliable ribbon-like or strip-like filaments.
Figure 16B:
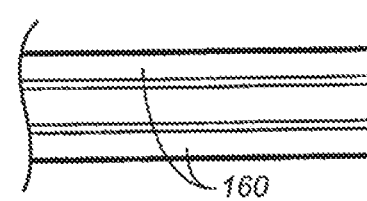
Figure 16C:
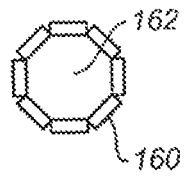

The ostial member may be of various designs. In some variations, the ostial member is formed form a one or more pliable filaments. For example, in FIG. 8A, ostial member 148 is formed from a single pliable filament 150 configured as an expandable coiled filament or wire which may be varied in its pitch, number and density of coils, coil linear and non-linear or patterned architecture and other like features. FIG. 8B shows the corkscrew ostial member 148 positioned within an ostium, and FIG. 8C shows an end view ostial member 148. Lumen 151 allows flow of mucus out of the sinus cavity. Ostial member 148 is adapted to be laterally compressible and/or bendable as shown by the arrows in FIG. 8B, in which case the coil diameter will increase or decrease. In another variation, as shown in FIG. 15A, a plurality of filaments 154, which may be tubular filaments (having lumens), are attached to form tubular ostial member 152. FIG. 15B shows the tubular ostial member 152 within a sinus ostium and FIG. 15C shows an end view of the ostial member 152. Lumen 156 allows flow of mucus out of the sinus cavity, as would the lumens of any tubular filament(s) if used in its construction. The ostial member 158 shown in FIGS. 16A-16C is similar to that in FIGS. 15A-15C except that the filaments 160 are formed as strips. Ostial member 158 also has a lumen 162 that permits mucus to flow from the sinus cavity to into the nasal passage.

In other variations, the ostial member is formed from a film or sheet-like material. For example, in FIG. 9A, ostial member 164 is formed from a pleated sheet (or alternatively from a plurality of tubular ring structures linked together) 166 configured as a reversibly compressible and/or bendable (as indicated by arrows in FIG. 9B) accordion-like tubular structure. FIG. 9B depicts ostial member 164 within a sinus ostium, and FIG. 9C shows an end view of ostial member 164. Lumen 168 allows flow of mucus out of the sinus cavity. Referring now to FIG. 10A, ostial member 170 includes a plurality of shaped apertures 172 cut out or punched out from film or sheet material 174, creating a non-woven mesh Although the apertures are shown as hexagonal in shape, it is understood that various other aperture shapes may be used. For example, the apertures 172 may be triangles, squares, octagons, diamonds, etc. FIG. 10B shows ostial member 170 within a sinus ostium. In FIG. 10C, it is shown how an ostial member of this design allow mucus to flow out through lumen 176 as well as through apertures 172 (see direction of arrows). Ostial member 170 may be also be formed to be compressible, expandable, bendable, and the like. Referring to FIGS. 12A-12C, 14A-14C, and 13A-13C, the film or sheet-like material 176 may also be configured to form a simple tube 178, a tubular hexagon 180, and a furled tube 182. Lumens 184, 186, and 188 allow passage of mucus from the sinus cavity to the nasal passage. Pressure may be applied in the direction of the arrows to the furled tube 182 in FIG. 13C to adjust the diameter of lumen 188.

In another variation, the ostial member 164 is formed from a plurality of sheets or strip-like filaments 166 configured as a star or asterisk-like structure. Spaces 168 between each strip allow mucus to flow past the ostial member 164 and optionally through a central lumen 165. FIG. 11B shows ostial member 164 within a sinus ostium, and FIG. 11C depicts an end view of ostial member 164. Further variations are illustrated in FIGS. 17-19. Referring to FIGS. 17A-17C, tubular ostial member 190 (top) is formed from a corrugated or pleated film or sheet 192. The ostial member 190 may be expanded in the direction of the arrows (shown in FIG. 17C) to form an ostial member of larger diameter 194. In FIGS. 18A-18C, the tubular ostial member 196 is made from gelfoam 198, with a pierced lumen 199, which may or not be supported by the addition of a tube. The ostial member 200 in FIGS. 19A-19C is a solid but porous cylinder 204 having a plurality of lumens 202. Lumens 202 extend through the tubular ostial member 200, either directly (as in a tube) or indirectly by connection through other internal cavities and/or lumens (not shown) such that mucus may pass out the end walls 206 and outer wall 208 of cylinder 204.

The ostial member may be formed to be rigid or flexible, and may also be formed to be coated with drug, coated with microencapsulated drug, or made as a polymer matrix with dispersed or dissolved drug. The drug included with the ostial member may be the same or different from that delivered by the expandable cavity member. The ostial member may be made from a biodegradable or nonbiodegradable polymer, a metal, or combinations thereof.

The dimensions of the ostial member will generally vary with the intended sinus of deployment. For example, for the maxillary sinus, the length of the ostial member may be less than 2 mm, but is usually between about 2 mm to about 6 mm, more usually between about 2 mm to about 5 mm, and more usually still between about 2 mm to about 4 mm. The outer diameter of the maxillary ostial member is usually between about 5 mm to about 10 mm, more usually between about 5 mm to about 9 mm, and more usually still between about 8 mm to about 10 mm. The internal diameter of the maxillary ostial member is usually between about 3 mm to about 9 mm, more usually between about 3 mm to about 8 mm, and more usually still between about 3 mm to about 7 mm.

For the frontal sinus, the length of the ostial member may be between about 0.5 mm to about 5 cm, between about 0.5 cm to about 4 cm, between about 0.5 cm to about 3 cm, between about 0.5 cm to about 2 cm, or between about 0.5 cm to about 1 cm. The outer diameter of the ostial member is usually about 5 mm, and the internal diameter about 3 mm. However, the inner and outer diameters may be smaller, especially in the instance where anchoring of the device is accomplished by the cavity member or nasal portion.

Nasal Portion.

The paranasal sinus devices of the invention may include a nasal portion, e.g., a nasal plate 210 (FIG. 20D), to aid in maintaining the position of the ostial member at the sinus ostium, or as an aid in reducing turbinate lateralization, possible occlusion of the middle meatus around the ostia, and tissue adhesions. If included, the nasal portion (e.g., element 46 in FIGS. 5A-5B and element 232 in FIG. 21) is secured to the proximal end of the ostial member to extend into the nasal passage, and may lie against the nasal mucosa.

Figure 20C:
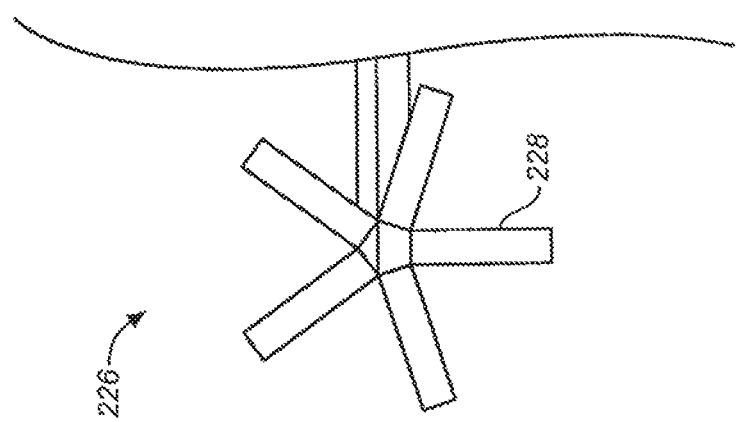
FIGS. 20A-20F illustrate various nasal portion configurations.
Figure 20B:
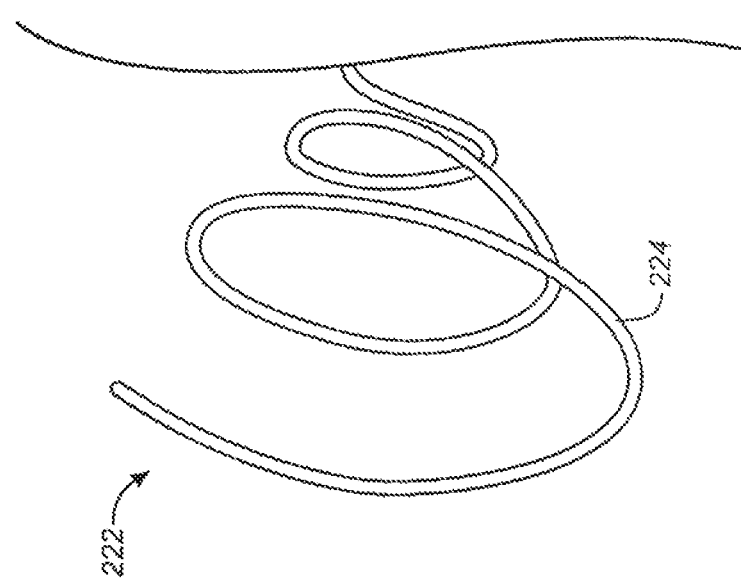
Figure 20A:
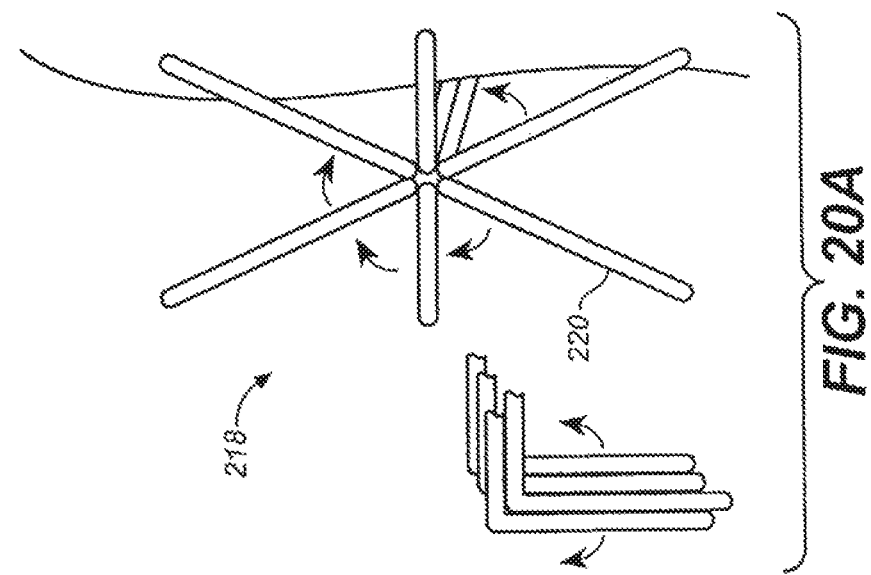
Figure 20F:
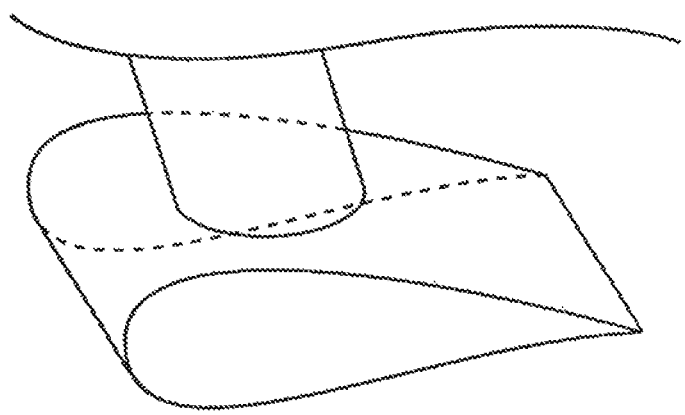
Figure 20E:
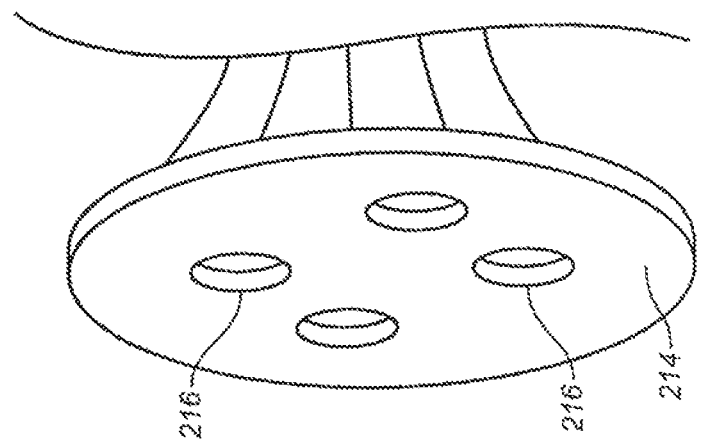
Figure 20D:
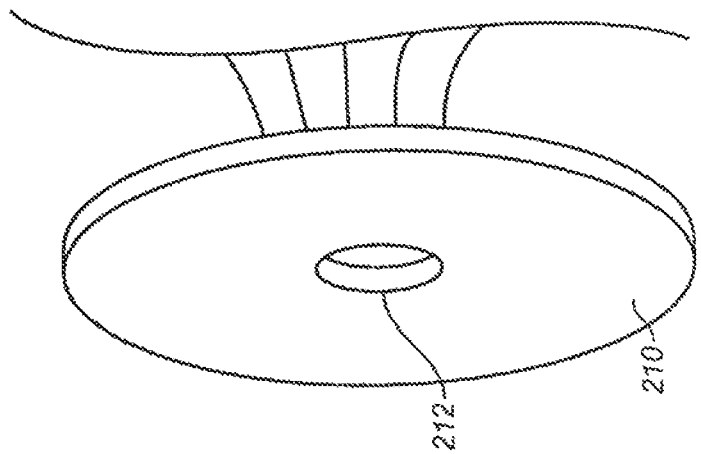

The nasal portion is configured to have at least one opening through which mucus flowing from the ostial member can drain into the nasal passage. The opening may be eccentrically located, or formed to be in the center of the nasal portion. In FIG. 20D, opening 212 is in the center of nasal plate 210. In FIG. 20E, nasal plate 214 has a plurality of openings 216 that allow drainage of mucus from the sinus into the nasal passage.

In other variations, the nasal portion is configured from one or more pliable filaments. Referring to FIG. 20A, nasal portion 218 is formed from a plurality of filaments 220 configured as radially extending spokes, which may be inserted as a more compact bundle of aligned parallel spokes, then deployed or unfurled so as to encircle the insertion point (see arrows and insertion view). Similarly, in FIG. 20C, nasal portion 226 is formed from a plurality of strip-like filaments 228. In FIG. 20B, nasal portion 222 is formed from a single pliable filament 224 configured as a spiral/helical structure. Another exemplary nasal portion is depicted in FIG. 20F, which comprises a compressible woven or nonwoven fold of sheeted material in the form of a wing-shaped tube, intended to adjustably conform to and support the middle meatus space and turbinate anatomy directly outside of an ostium.

The nasal portion may be formed to be rigid, flexible, or self-expanding, and may also be formed to be coated with drug, coated with microencapsulated drug, or made as a polymer matrix with dispersed or dissolved drug within the polymer matrix. The drug included with the nasal portion may be the same or different from that delivered by the cavity member. The nasal portion may be made from a biodegradable or nonbiodegradable polymer, a metal, or combinations thereof.

The shape of the nasal portion may also vary depending on such factors as the sinus of deployment and whether additional sinuses, e.g., the ethmoid sinus, are to be treated. For example, in an individual needing treatment for both maxillary and ethmoid sinus inflammation, a maxillary paranasal sinus device having a nasal portion shaped to contact a portion of the ethmoid air cells is particularly desirable.

The paranasal sinus devices may include any combination of the aforementioned cavity members, ostial members, and nasal portions. For example, as shown in FIG. 21, device may include a multiple looped cavity member 228 (previously described for FIG. 7D) and a tubular ostial member (previously described for FIG. 15A). Nasal portion 232 is also formed from a plurality of filaments 234 configured as splayed prongs. Each component of the device, i.e., the cavity member, ostial member, and nasal portion, may be formed contiguously (each filament, tube, sheet, or film forms all components) or separately, and then attached by methods previously described. Each component may also be perforated, contain pores, or have other structural or surface features which enhance or alternatively prevent impedance of mucociliary clearance, and aid in the placement and deployment of the device.

Figure 22A:
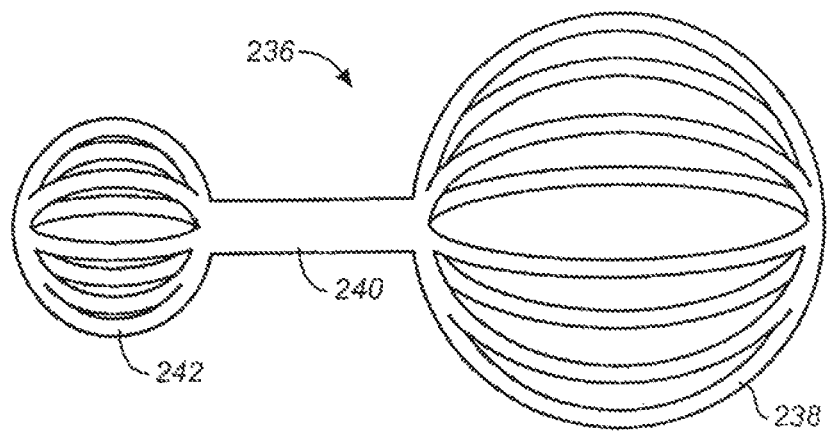
FIGS. 22A-22C show perspective, side cross-sectional, and end views of a paranasal sinus device having a cavity member and nasal portion formed from multiple loops of pliable filaments.
Figure 22B:
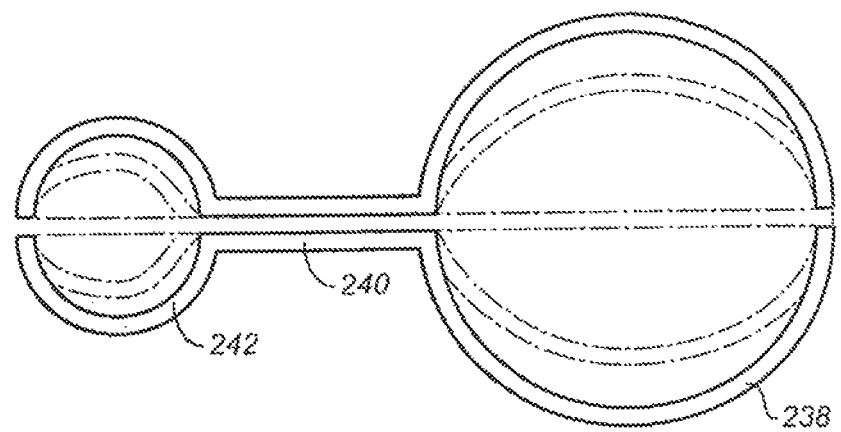
Figure 22C:
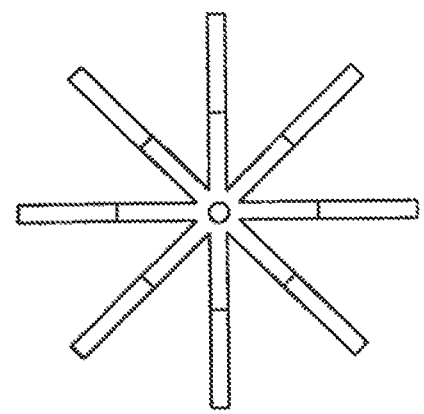

In another variation, paranasal sinus device 236 includes a whisk-like cavity member 238 (previously described for FIG. 7F), a tubular ostial member 240 (previously described for FIG. 14A), and another whisk-like component 242 similar to cavity member 238 as the nasal portion 242. FIG. 22C shows an end view from the nasal portion of the device.

Figure 23A:
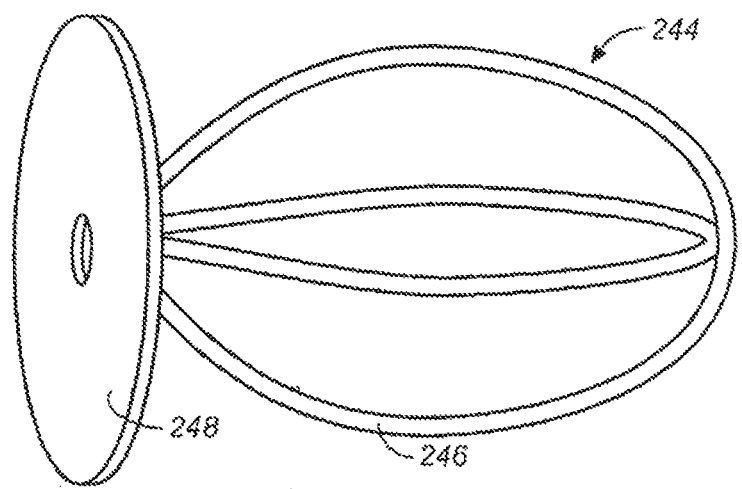
FIGS. 23A-23C show perspective, side cross-sectional, and end views of a paranasal sinus device having a looped cavity member and a nasal plate.
Figure 23B:
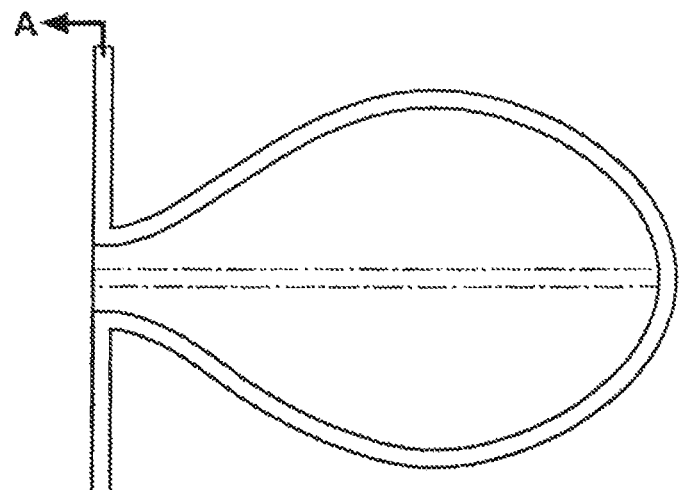
Figure 23C:
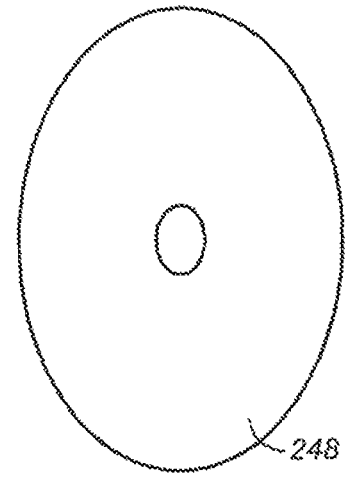

In a further variation, shown in FIGS. 23A-23C, paranasal sinus device 244 includes a multiple looped cavity member 246 (previously described for FIG. 7D) and a nasal plate 248 (previously described for FIG. 20D. FIG. 23B is a side cross-sectional view of device 244 and an cross-section end view through line A-A is shown in FIG. 23C.

Active Agents.

Any active agent may be included in the devices described herein so long as they are suitable to treat a paranasal sinus condition and are capable of achieving the desired release kinetics. The active agents that may be used in a paranasal sinus device to treat a paranasal sinus condition include, but are not limited to, anticholinergic agents, antihistamines, anti-infective agents, anti-inflammatory agents, antiscarring or antiproliferative agents, chemotherapeutic/antineoplastic agents, cytokines such as interfereon and interleukins, decongestants, healing promotion agents and vitamins (e.g., retinoic acid, vitamin A, and their derivatives), hyperosmolar agents, immunomodulator/immunosuppressive agents, leukotriene modifiers, mucolytics, narcotic analgesics, small molecules, tyrosine kinase inhibitors, peptides, proteins, nucleic acids, vasoconstrictors, or combinations thereof. Anti-sense nucleic acid oligomers or other direct transactivation and/or transrepression modifiers of mRNA expression, transcription, and protein production may also be used. Anti-infective agents generally include antibacterial agents, antifungal agents, antiparasitic agents, antiviral agents, and antiseptics. Anti-inflammatory agents generally include steroidal and nonsteroidal anti-inflammatory agents.

Examples of antibacterial agents that may be suitable for use with the described methods and devices include, but are not limited to, aminoglycosides, amphenicols, ansamycins, β-lactams, lincosamides, macrolides, nitrofurans, quinolones, sulfonamides, sulfones, tetracyclines, vancomycin, and any of their derivatives, or combinations thereof. In one variation, β-lactams are the preferred antibacterial agents.

β-lactams that may be suitable for use with the described methods and devices include, but are not limited to, carbacephems, carbapenems, cephalosporins, cephamycins, monobactams, oxacephems, penicillins, and any of their derivatives. In one variation, penicillins (and their corresponding salts) are the preferred β-lactams.

The penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, amoxicillin may be included in the paranasal sinus device. In another variation, the device includes ampicillin. Penicillins combined with clavulanic acid such as Augmentin® (amoxicillin and clavulanic acid) may also be used.

Examples of antifungal agents suitable for use with the described methods and devices include, but are not limited to, allylamines, imidazoles, polyenes, thiocarbamates, triazoles, and any of their derivatives. In one variation, imidazoles are the preferred antifungal agents. Antiparasitic agents that may be employed include such agents as atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet--hoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami--de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N--,N-bis(2-carbamoylethyl)-sulfonilimino]-1,3,5-triazin-2-ylamino-biphenyl--2-,2'-disulfonic acid disodium salt), BABIM (Bis[5-Amidino-2-benzimidazoly-1]-methane), NIH351, and combinations thereof.

Typically, if inclusion of an anti-inflammatory agent is desired, a steroidal anti-inflammatory agent, e.g., a corticosteroid, is employed. Examples of steroidal anti-inflammatory agents that may be used in the devices include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In one variation, budesonide is included in the device as the steroidal anti-inflammatory agent. In another variation, the steroidal anti-inflammatory agent may be mometasone furoate. In yet another variation, the steroidal anti-inflammatory agent may be beclomethasone. In yet a further variation, the steroidal anti-inflammatory agent may be fluticasone propionate.

If a nonsteroidal anti-inflammatory agent is used, suitable agents include, but are not limited to, COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide).

The chemotherapeutic/antineoplastic agents that may be used in the paranasal sinus devices include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, *bacillus* calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, analogs/congeners, derivatives of such compounds, and combinations thereof.

Exemplary decongestants that may be incorporated in the paranasal sinus devices, include, but are not limited to, epinephrine, pseudoephedrine, oxymetazoline, phenylephrine, tetrahydrozolidine, and xylometazoline. Mucolytics that may be used include, but are not limted to, acetylcysteine, dornase alpha, and guaifenesin. Anti-histamines such as azelastine, diphenhydramine, and loratidine may also be used.

In those instances where it is desirable to remove water from tissue, e.g, to remove fluid from polyps or edematous tissue, a hyperosmolar agent may be employed. Suitable hyperosmolar agents include, but are not limited to, furosemide, sodium chloride gel, or other salt preparations that draw water from tissue or substances that directly or indirectly change the osmolar content of the mucous layer.

The active agent may constitute from about 0.01% to about 95%, 0.01% to about 95%, from about 0.01% to about 90%, from about 0.01% to about 80%, from about 0.01% to about 70%, from about 0.01% to about 60%, from about 0.01% to about 50%, from about 0.01% to about 40%, from about 0.01% to about 30%, from about 0.01% to about 20%, from about 0.01% to about 10%, from about 0.01% to about 5%, from about 0.01% to about 1%, or from about 0.01% to about 0.25% by weight of the releasing portion (e.g., the cavity member, ostial member, and/or nasal portion) or releasing material (e.g., layer or layers having the active agent) of the device. The amount of active agent used will usually depend on factors such as the particular agent incorporated, the paranasal sinus condition being treated, and the severity of clinical symptoms, but in all instances will usually be an amount that is effective for treating the paranasal sinus condition upon delivery into a sinus. For example, when treating paranasal sinus inflammation, the device may be formed to deliver per day, from about 1 µg to about 100 µg, from about 10 µg to about 50 µg, from about 10 µg to about 40 µg, from about 10 µg to about 30 µg, from about 10 µg to about 25 µg, or from about 10 µg to about 20 µg of mometasone furoate into the sinus. In another variation, the device may be formed to deliver per day, from about 10 µg to about 700 µg, from about 25 µg to about 400 µg, from about 75 µg to about 300 µg, or about 100 to about 200 µg of fluticasone propionate into the sinus. In some instances, crystal forms, e.g., hydrous and anhydrous crystal forms, of drugs may be used in the methods and devices described here. For example, mometasone furoate monohydrate may be used.

The active agent may be incorporated and released from the cavity member, ostial member, and/or the nasal portion. In another variation, the active agent may be coated onto the surface of the cavity member, ostial member, and/or the nasal portion. An exemplary way the coating may be achieved is by dissolving or suspending the active agent in a solution or melt of a biodegradable or nonbiodegradable polymer. In another exemplary way, the active agent may be powder coated onto the surface of the filament that has been made adhesive by, e.g., heating or softening with a solvent or plasticizer. In yet another variation, microencapsulated drug may be attached to the surface of the cavity member, ostial member, and/or the nasal portion. As previously mentioned, the active agent may be incorporated throughout all portions of the device or in particular portions of the device (e.g., the cavity member and ostial member, nasal portion and cavity member, etc.).

The active agent may be included in the device such that differential release results. The differential release may be of the same active agent or for different active agents. For example, variable release of a single active agent may be achieved using methods such as bulk loading, surface coating (e.g., by having a higher load layer), surface loading (e.g., by embedding, spraying, or absorbing drug onto the device surface, etc.), and other techniques well known in the art. Variable release of different active agents may be achieved, e.g., by segmenting the drugs into different layers, reservoirs and/or microspheres, which themselves may have differing permeability or biodegradation profiles, as well as by other techniques well known in the art.

Polymers.

When the devices are made with polymers, selection of the biodegradable or nonbiodegradable polymer to be employed will vary depending on the residence time and release kinetics desired, method of device delivery, particular therapeutic agent used, and the like. In all instances, the biodegradable polymer when degraded results in physiologically acceptable degradation products. The biodegradable or nonbiodegradable polymer may constitute at least about 5%, at least about 10%, at least about 20%, at least about 30%, at least about 40%, at least about 50%, at least about 60%, at least about 70%, at least about 80%, at least about 90%, at least about 95%, or at least about 100% by weight of the device or component that it makes (e.g., sinus cavity member, ostial member, or nasal portion).

Suitable biodegradable and biocompatible polymers for use in making the paranasal sinus devices include, but are not limited to, polymers such as a poly(lactide); a poly (glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly (caprolactone); poly(caprolactone)/poly(ethylene glycol) copolymers a poly(orthoester); a poly(phosphazene); a poly (hydroxybutyrate) or a copolymer including a poly(hydroxybutyrate); a poly(lactide-co-caprolactone); a polycarbonate; a polyesteramide; a polyanhydride; a poly (dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof. Biodegradable shape memory polymers, such as those commercialized by nmemoScience in Aachen, Germany, or those described in U.S. Pat. Nos. 5,189,110 or 5,139,832, may also be employed.

As used herein, a poly(lactide); a poly(glycolide); a poly(lactide-co-glycolide); a poly(lactic acid); a poly(glycolic acid); a poly(lactic acid-co-glycolic acid) will all be referred to as PLG, PLG polymers, or lactide/glycolide polymers. Lactide/glycolide polymers for the drug delivery devices and compositions of this invention are typically made by melt polymerization through the ring opening of lactide and glycolide monomers. Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. In one variation, linear lactide/glycolide polymers are used; however, star polymers may be used as well. In other variations, high molecular weight polymers may be used to form the devices of this invention, for example, to meet strength requirements and extend bioabsorption time. In other instances, low molecular weight polymers may be used when resorption time and not material strength is important. The lactide portion of the polymer has an asymmetric carbon. Racemic DL-, L-, and D-polymers are commercially available to include in the devices of this invention. The L-polymers are more crystalline and resorb slower than DL-polymers. In addition to copolymers comprising glycolide and DL-lactide or L-lactide, copolymers of L-lactide and DL-lactide are also commercially available. Additionally, homopolymers of lactide or glycolide are commercially available. Star polymers of lactide or glycolide or lactide/glycolide copolymers are also commercially available.

In the case when the biodegradable polymer is poly (lactide-co-glycolide), poly(lactide), or poly(glycolide), the amount of lactide and/or glycolide in the polymer may vary. In one variation, the biodegradable polymer contains from about 0 to about 100 mole %, from about 40 to about 100 mole %, from about 50 to about 100 mole %, from about 60 to about 100 mole %, from about 70 to about 100 mole %, or from about 80 to about 100 mole % lactide, and from about 0 to about 100 mole %, from about 0 to about 60 mole %, from about 10 to about 40 mole %, from about 20 to about 40 mole %, or from about 30 to about 40 mole % glycolide, wherein the amount of lactide and glycolide is 100 mole %. In other variations, the biodegradable polymer may be poly(lactide), about 85:15 poly(lactide-co-glycolide), about 75:25 poly(lactide-co-glycolide), about 65:35 poly(lactide-co-glycolide), or about 50:50 poly(lactide-co-glycolide), where the ratios are mole ratios.

In another variation, when the biodegradable polymer is poly(lactide-co-glycolide), poly(lactide), or poly(glycolide), the polymer has an intrinsic viscosity of from about 0.15 to about 1.5 dL/g, from about 0.25 to about 1.5 dL/g, from about 0.25 to about 1.0 dL/g, from about 0.25 to about 0.8 dL/g, from about 0.25 to about 0.6 dL/g, or from about 0.25 to about 0.4 dL/g as measured in chloroform at a concentration of 0.5 g/dL at 30° C.

If a nonbiodegradable polymer is used to make or incorporate into the device or composition, suitable nonbiodegradable polymers include, but are not limited to, poly (ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly (vinyl imidazole), chorosulphonated polyolefins, polyethylene oxide, and copolymers and blends thereof.

Furthermore, the devices may be made from any biocompatible, biodegradable or nonbiodegradable polymer that is mucoadhesive. In some instances, the cavity member, ostial member, and/or nasal plate may be coated with a mucoadhesive, which may or may not be a polymer. The devices may also be made from a polymer that carries a charge.

In another variation, natural polymers may be used. Representative natural polymers that may be included in the devices include, but are not limited to, proteins, such as zein, modified zein, casein, chitin, gelatin, gluten, serum albumin, or collagen, and polysaccharides, such as cellulose, dextrans, and polyhyaluronic acid. Hydrogel or sol-gel mixtures of polysaccharides are may also be employed.

Other Materials.

In some variations, the devices may be made from a metal. Examples of suitable metals include, but are not limited to, cobalt, chromium, nickel, platinum, stainless steel, titanium, tantalum, and any of their alloys, e.g., nickel-titanium alloys, and combinations thereof.

Additional Agents.

The devices and compositions of this invention may further include components such as preservatives, buffers, binders, disintegrants, lubricants, and any other excipients necessary to maintain the structure and/or function of the devices. For example, the pliable filaments may be formed to contain a plasticizer or solvent such as acetone, methyl ethyl ketone, ethyl lactate, ethyl acetate, dichloromethane, or ethyl acetate/alcohol blends that would soften the biodegradable or nonbiodegradable polymer of the device. The plasticizer or solvent would diffuse or otherwise be released from the device into the sinus mucosa after deployment and expansion of the cavity member to harden the polymeric filaments (of the device) such that the device substantially conforms to the shape of the sinus cavity, and to the extent that a better friction fit of the cavity member against the sinus cavity wall is provided.

Furthermore, as previously described, the pliable filaments may also include a mucoadhesive polymer to enhance contact of the cavity member to the sinus mucosa. Examples of mucoadhesive polymers that may be employed include homopolymers of acrylic acid monomers such as polyacrylic acid and any of its pharmaceutically acceptable salts; copolymers of acrylic acid and methacrylic acid, styrene, or vinyl ethers; vinyl polymers such as polyhydroxyethyl acrylate, polyhydroxyethyl methacrylate, polyvinyl alcohol, and polyvinyl pyrrolidone; cellulosic derivatives such as methyl cellulose, ethyl cellulose, hydroxyethyl cellulose, hydroxypropyl cellulose, hydroxypropylmethyl cellulose, and carboxymethyl cellulose; polysaccharides such as alginic acid, sodium alginate, and tragacanth gum; collagen; gelatin; and any combination thereof.

Release Kinetics.

The devices described here may be formulated with particles of an active agent dispersed or dissolved within a biodegradable polymer matrix, and formulated to provide sustained release of the active agent. If made from a non-swellable polymer, e.g., lactide/glycolide polymers, release of the active agent from the matrix is most likely achieved by erosion of the biodegradable polymer matrix and/or by diffusion of the active agent into the mucous layer of the sinus. Factors that may influence the release kinetics include such characteristics as the size of the active agent particles, the solubility of the active agent, the ratio of active agent to polymer(s), the porosity of the polymer, the method of device manufacture, the exposed surface area of the device, the surface area to volume ratio of the device, and the erosion rate of the matrix polymer(s).

The active agent may be released from the device over a prolonged time period including, but not limited to, at least about one week, at least about two weeks, at least about three weeks, or at least about four weeks, at least about two months, at least about three months, at least about four months, at least about five months, or at least about six months or more. In one variation, the therapeutic agent is released over about two weeks to about four weeks.

The drug release profile of the paranasal sinus devices may be adjusted by various techniques, such as through use of different drug, polymer, and excipient formulations or adjustment of their amounts in the formulations, use of release and drug barrier layers, differential bead, microsphere, or microcapsule constructions (with shells of varying molecular weights or thicknesses), and the like, as is well known in the art. The duration of release can also be adjusted through polymer blending ratios, monomer average molecular weights, and coatings.

As previously mentioned, differential release of the drug(s) may also be effected. The differential release may be of the same active agent or for different active agents. For example, variable release of a single active agent may be achieved using methods such as bulk loading, surface coating (e.g., by having a higher load layer), surface loading (e.g., by embedding, spraying, or absorbing drug onto the device surface, etc.), and other techniques well known in the art. Variable release of different active agents may be achieved, e.g., by segmenting the drugs into different layers, reservoirs and/or microspheres, as well as by other techniques well known in the art.

Figure 24A:
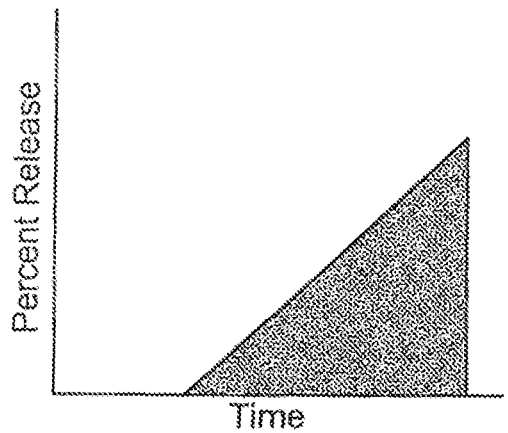
FIGS. 24A-24F show exemplary drug release curves for the paranasal sinus devices.

Delayed drug release, as shown in FIG. 24A is useful for adjunctive therapy, as when tapering off of intravenous or oral steroids previously given to a patient, or when releasing anti-scarring and anti-restenosis agents later in the healing process.

Figure 24B:
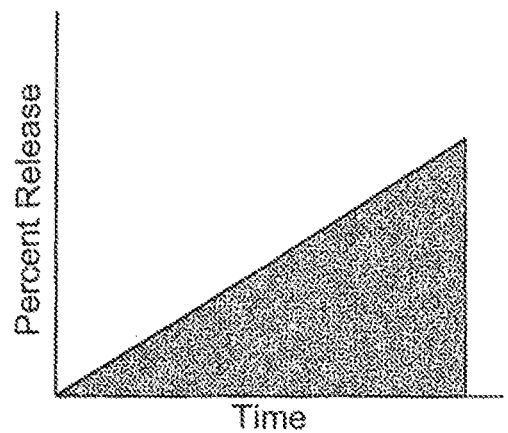

Substantially zero order drug release, as shown in FIG. 24B is useful for chronic disease maintenance therapy without trauma or scarring, or for anti-infective agent courses of therapy, providing a constant equilibrium concentration of drug and maximizing receptor target occupation levels.

Figure 24C:
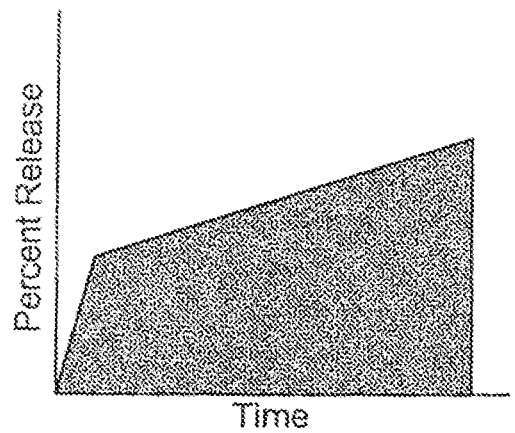

Upfront bolus drug release, as shown in FIG. 24C during the first five to ten days is useful for treatment of post-surgical or implant insertion trauma and for creating maximum diffusion into the adjacent surgical anatomy.

Figure 24D:
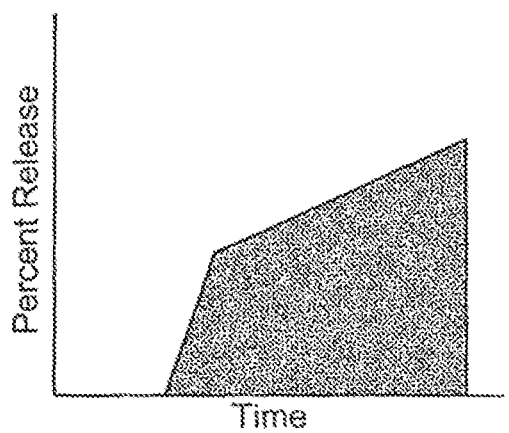

Delayed bolus drug release, as shown in FIG. 24D is useful in post-operative treatment, particularly amelioration of trauma in post-operative debridement therapy.

Figure 24E:
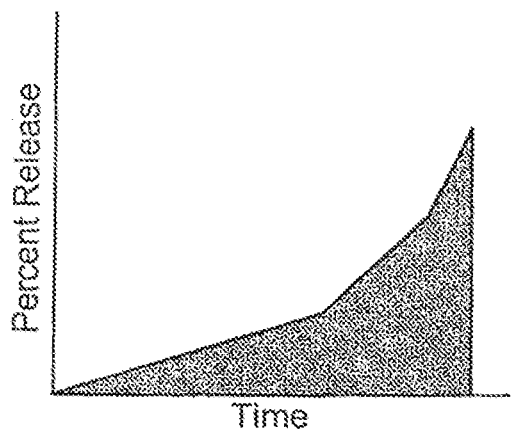

Degradation dependent release, as shown in FIG. 24E, increasing as the device is fully bioabsorbed, is useful for prevention of any implant/device elimination trauma or complications due to bioabsorption.

Figure 24F:
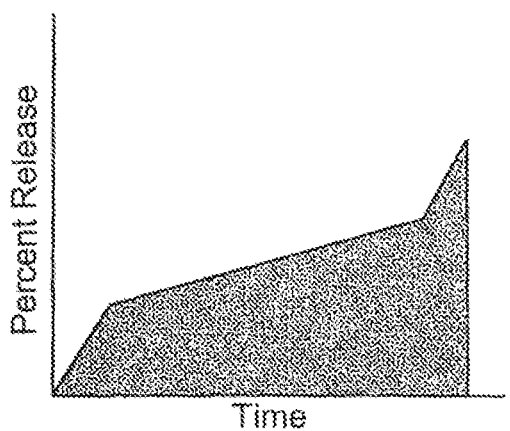

Combinations are possible of any of the above drug release curves by integrating various drug release methods (for one or more drugs) in a single device. For example, as illustrated in FIG. 24F, a combination of an initial bolus, followed by substantially zero order release, followed by a final release burst is particularly useful in post-surgical application of the device, treating surgical and implantation trauma (initial bolus) then surgical healing and disease recurrence (substantially zero order), and ultimately any implant elimination trauma (final release burst).

Applications.

Therapeutic Action of Device.

The structure of the paranasal sinus device itself may also have a therapeutic function. For example, the device may provide such functions as fixation or splinting tissue via space filling, fastening, deflection, in order to provide support and to keep a body structure open, as in stenting or packing to prevent the lateralization of the middle turbinate and occlusion of the middle meatus, or by providing a physical barrier to adhesions which may form between various post-surgical and/or inflamed tissue surfaces. For example, any device incorporating a solid, semi-solid (gel) or woven or nonwoven mesh structure could be used to practice this method. In another variation, the device may non-occlusively maintain patency through the implant feature area providing the device action by direct provision and maintenance of a channel, fenestration or port from the sinuses to the infundibulum, osteomeatal complex, meatus or nasal passage by which mucociliary flow may travel. Such a channel may be within and support the structure of natural ostia or within and support a surgically created or modified antrostomy to the sinus, but may not totally occlude such openings. For example, any device with a lumen or pore such as a tube or cannula, or stent with a lumen, could be used to practice this method, as could a highly porous packing material, three dimensional mesh, or surface or interior structured device through which mucus can flow and which does not become occlusive of the provided channel through absorbancy, expansion, or degradation.

Reduction of Complications Upon Implantation.

In yet another variation, the device may possess a structural feature or active agent that helps to reduce the complications of device implantation. For example, the device may: 1) prevent trauma due to device removal by use of bioabsorbable materials; 2) prevent biofilm formation by use of coatings, physical surface treatments, and/or incorporation or elution of an anti-infective or antiseptic substance; 3) prevent foreign body reactions by incorporating low-dose anti-inflammatory substances including steroidal and non-steroidal anti-inflammatories (for example, including the anti-inflammatory effects of low dose macrolide antibiotics); and 4) prevent device migration by specific active or passive fixation and anchoring features incorporated in the device. Substances that may be used to prevent biofilm formation include, but are not limited to, alcohol, chlorhexidine, iodine, triclosan, hexachlorophene, and silver-based agents (e.g., silver chloride, silver oxide, silver nanoparticles). In other variations, the surface of the device may treated by a process (e.g. ion embedding, plasma etching, etc.) altering the physical properties of the surface of the device in order to prevent biofilm formation.

Exploitation of Mucociliary Clearance.

Normal mucociliary clearance may be used to extend drug diffusion and effect beyond the physical location of the device. This is useful in both normal and particularly diseased mucociliary flow patterns. In the later case, the device is useful in effecting the build up of therapeutically desirable concentrations of released drug at blockages when the normal mucociliary flow is interrupted or impeded by disease, and increasing drug concentration gradients where mucociliary function is most impacted by disease. Anatomical blockages and areas of mucociliary dysfunction or ciliary dysmotility may be particularly desirable areas of such drug treatments (e.g., anti-inflammatories and anti-infectives, but also including chemotherapeutic agents), so as to "chemically open" the blockage and to increase treatment of the damaged mucosa. Thus, the natural sinus and upstream locations along the mucociliary clearance pathway may serve as drug depots, with drug traveling to desired sites downstream in the pathway. This contrasts with previous and current teachings in the field which seek to impede or reduce mucociliary clearance of active agents in order to maximize dose duration.

In addition to treating any one of the aforementioned paranasal sinus conditions, the devices described herein may be placed during, or as an adjunct to, a surgical, non-surgical, or other therapeutic intervention of the sinuses or nasal passages. For example, the device may be used during or as an adjunct to such procedures including, but not limited to, septoplasty (surgical removal or adjustment of the nasal septum); turbinoplasty (surgical removal or adjustment of the turbinate bones); rhinoplasty generally; sinus surgery (including the exploration, revision, repair, tissue dissection or removal of some or part of any of the sinuses, including the ethmoid sinuses (as in ethmoidectomy), maxillary sinuses, frontal sinuses, or sphenoid sinuses); polyp removal in any part of the paranasal sinuses and nasal passages; cannulation, irrigation, and therapy instillation or injection of any of the above sinuses or the nasal passages, including through nasal, trans-ostial, and external puncture approaches (such as through antral puncture, trephination or "Caldwell-Luc" procedures); surgical revision, dissection, reconstruction or repair of the anatomy of the paranasal sinuses and nasal passages, including any removal or adjustment of neoplasms, foreign bodies, lesions, adhesions, defects, stenosis, and fistula of the natural or post-surgical anatomy; ligation, cauterization, and ablation procedures to control nasal bleeding and repair vasculature in the anatomy of the paranasal sinuses and nasal passages, or as an adjunct or technique to perform any such surgical or non-surgical procedure.

Thus, the devices described here may have a variety of functions. For example, they may deliver an active agent to treat rhinosinusitis, have a structure that prevents lateralization of the middle turbinate and formation of adhesions, have a structure which directly or indirectly preserves ostial patency, as well as have a coating that prevents biofilm formation. The devices may be formed to include any number and combination of functions listed above.

Delivery Devices and Methods of Use.

The paranasal sinus devices may be placed into the sinus using various types of sinus inserters. The inserter may include a conduit, e.g., a catheter with a lumen. The conduit may be flexible or rigid, or may be designed to have varying degrees of stiffness along its length, e.g., the distal portion of the conduit may be stiffer than the proximal portion. In addition, the distal portion of the conduit may be variously angulated to facilitate positioning and advancement of the conduit through the sinus ostium. For example, the distal portion may be angulated from about 0° to about 175°, from about 0° to about 135°, or from about 0° to about 90°. If desired, the distal portion of the conduit may also be formed to be malleable.

The conduit may be made from any biocompatible material including, but not limited to, stainless steel and any of its alloys; titanium alloys, e.g., nickel-titanium alloys; polymers, e.g., polyethylene and copolymers thereof, polyethylene terephthalate or copolymers thereof, nylon, silicone, polyurethanes, fluoropolymers, poly(vinylchloride), and combinations thereof, depending on the amount of flexibility or stiffness desired.

The inserter may be preloaded with a single paranasal sinus device on or within the distal end of the conduit, but more than one device may be preloaded if desired. It may be preloaded on or within the inserter by the physician prior to insertion or preloaded on or within the inserter during the manufacturing process. Once access through a sinus ostium or surgically created fenestration has been obtained with the conduit, the sheath may be retracted to slidably deploy the nasal portion of the device. If the cavity member is self-expanding, then retraction of a sheath also causes the cavity member to be deployed. If expansion using a balloon is required, any balloon catheter (including double balloon catheters) known in the art may be advanced through the lumen in the conduit until the balloon lies within the cavity member. Inflation of the balloon thereby causes the cavity member to change from a first collapsed configuration to a second expanded configuration and contact the sinus cavity wall. An endoscope may also be used while positioning the inserter to aid with visualization of the ostium. Irrigation tools and electrocautery may also be employed if needed.

The following description provides an exemplary way of a how a single device might be deployed into a sinus using a sinus inserter. The sinus inserter typically includes a distal portion, a sinus device in its collapsed configuration on the distal portion, a handle, a conduit having a lumen, and a sheath connected to a retractable knob. Upon pulling the retractable knob, the knob moves proximally to abut the handle and slidably deploy the self-expanding nasal plate of the device. A balloon catheter may then be advanced through the lumen of the conduit into the distal portion of the inserter and inflated to expand the sinus device, such as the flexible mesh 40 of FIGS. 4A-4B.

Method of Manufacture.

The method of preparing the devices of this invention will generally depend on the particular active agent or polymer used, form of the cavity member, and the release kinetics desired, but may be made by any one of the numerous methods known in the art. For example, the devices may be made by such processes as extrusion; injection or form molding; blow, film, or melt casting; welding; and other manufacturing techniques well known in the art (e.g., cutting and annealing). The filaments may be wet or melt spun, formed by laser or other cutting, formed by slitting, formed by extrusion, injection or other molding, or casting.

EXAMPLES

The following examples serve to more fully describe the manner of making and using the above-described devices. It is understood that these examples in no way serve to limit the scope of this invention, but rather are presented for illustrative purposes.

Furthermore, the following examples will employ, unless otherwise indicated, conventional techniques of pharmaceutical formulation, medicinal chemistry, and the like, which are within the skill of the art. Such techniques are explained fully in the literature. Efforts have been made to ensure accuracy with respect to numbers (e.g., amounts, temperature, etc.), but some experimental error and deviation should be accounted for. Unless indicated otherwise, parts are parts by weight, temperature is in degrees Celsius (° C.) and pressure is at or near atmospheric pressure at sea level. All components are obtainable commercially unless otherwise indicated.

Example 1: Melt Extrusion of Fiber Containing 5 wt % Mometasone Furoate

Extruded ribbon fiber was made with mometasone furoate and poly(DL-lactide-co-glycolide). The desired mometasone furoate content in the device was 5 wt % mometasone furoate. The poly(DL-lactide-co-glycolide) was ester capped with a molar ratio of 70/30 DL-lactide/glycolide and had an inherent viscosity of 0.81 dL/g. The inherent viscosity was measured at 30° C. with 0.5 gm/dL polymer concentration in chloroform.

First mometasone furoate (0.5 gm) and the poly(DL-lactide-co-glycolide) (9.5 gm) were dissolved in methylene chloride (40 gm). A thin film was cast from the resulting solution. The cast film was dried in a vacuum oven for 48-96 hours to remove residual methylene chloride. The cast film was cut into thin strips approximately 10-20 mm wide and 100-150 mm long. Next a Tinius Olsen Model UE-4-78 melt plastometer was used to extrude the cast film strips. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a custom machined die was used with internal core dimensions of 0.3556 mm×2.0015 mm. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The cast film strips, approximately 4 gm, were loaded into the Tinius Olsen which had been equilibrated to 120° C. A charging rod was placed in the core of the Tinius Olsen to compress the blend and a weight of 10 kg was placed on the end of the charging rod to aid in the compaction of the blend. The equilibration time for the blend to melt lasted for about 20 minutes. After an extrusion load of 10,000 gm was placed on the charging rod, the plug was removed from the discharge area to begin the extrusion run. As the ribbon fiber was extruded from the discharge, it was pulled using a conveyor belt to the desired dimensions (0.3-0.4 mm×1.0-1.2 mm). The 4-gm charge afforded 7-10 segments of extruded fiber each having a length of about 100 cm.

Example 2: Melt Extrusion of Fiber Containing 5 wt % Mometasone Furoate and 2 wt % Triethyl Citrate Extruded ribbon fiber was made with mometasone furoate, triethyl citrate (plasticizer) and poly(DL-lactide-co-glycolide). The desired mometasone furoate content in the device was 5 wt % mometasone furoate. The poly(DL-lactide-co-glycolide) was ester capped with a molar ratio of 70/30 DL-lactide/glycolide and had an inherent viscosity of 0.81 dL/g. The inherent viscosity was measured at 30° C. with 0.5 gm/dL polymer concentration in chloroform.

First mometasone furoate (0.5 gm), triethyl citrate (0.2 gm) and the poly(DL-lactide-co-glycolide) (9.3 gm) were dissolved in ethyl acetate (40 gm). A thin film was cast from the resulting solution. The cast film was dried in a vacuum oven for 48-96 hours to remove residual methylene chloride. The cast film was cut into thin strips approximately 10-20 mm wide and 100-150 mm long. Next a Tinius Olsen Model UE-4-78 melt plastometer was used to extrude the cast film strips. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a custom machined die was used with internal core dimensions of 0.3556 mm×2.0015 mm. The main block of the Tinius Olsen has heater bands encased by insulation and a shroud that allow the Tinius Olsen to be heated to a desired temperature. A thermocouple was used to measure the temperature of the block. The control system then used the thermocouple values to either turn the heater bands on or off. Throughout the extrusion process, the heater bands switched off and on to maintain the desired temperature. The cast film strips, approximately 4 gm, were loaded into the Tinius Olsen which had been equilibrated to 120° C. A charging rod was placed in the core of the Tinius Olsen to compress the blend and a weight of 10 kg was placed on the end of the charging rod to aid in the compaction of the blend. The equilibration time for the blend to melt lasted for about 20 minutes. After an extrusion load of 10,000 gm was placed on the charging rod, the plug was removed from the discharge area to begin the extrusion run. As the ribbon fiber was extruded from the discharge, it was pulled using a conveyor belt to the desired dimensions (0.3-0.4 mm×1.0-1.2 mm). The 4-gm charge afforded 7-10 segments of extruded fiber each having a length of about 100 cm.

Various compositions of ribbon fiber were made following fabrication techniques similar to those described in Examples 1 and 2. Table 1 below lists these formulation compositions having varying amounts of mometasone furoate, plasticizers, and porosigens and showing the use of different processing solvents (ethyl acetate and methylene chloride) to prepare material to place into an extruder.

TABLE 1

Compositions of ribbon fibers prepared by melt extrusion

| Batch Number | Batch Size (g) | Polymer (DL-PLG) | Mometasone Load (wt %) | Processing Solvent | Plasticizer | Plasticizer Content (wt %) | Porosigen | Porosigen Content (wt %) | Fiber Dimensions Thickness (mm) | Fiber Dimensions Width (mm) |
|---|---|---|---|---|---|---|---|---|---|---|
| 0015-50 | 5 | 69:31 | 2 | Ethyl Acetate | TEC | 2 | NA | 0 | 0.4 | 1.50 |
| 0015-51 | 5 | 69:31 | 2 | Ethyl Acetate | TEC | 4 | NA | 0 | 0.50 | 1.45 |
| 0015-52 | 5 | 69:31 | 5 | Ethyl Acetate | TEC | 0 | NA | 0 | 0.36 | 1.00 |
| 0015-53 | 5 | 69:31 | 5 | Ethyl Acetate | TEC | 2 | NA | 0 | 0.52 | 1.45 |
| 0015-54 | 5 | 69:31 | 5 | Ethyl Acetate | TEC | 4 | NA | 0 | 0.56 | 1.50 |
| 0015-55 | 5 | 69:31 | 10 | Ethyl Acetate | TEC | 4 | NA | 0 | 0.50 | 1.30 |
| 0015-56 | 5 | 69:31 | 10 | Ethyl Acetate | TEC | 2 | NA | 0 | 0.50 | 1.38 |
| 0065-01 | 3.9 | 69:31 | 2 | Ethyl Acetate | TEC | 2 | NA | 0 | 0.53 | 1.33 |
| 0065-02 | 3.8 | 69:31 | 5 | Ethyl Acetate | TEC | 0 | NA | 0 | 0.38 | 1.28 |
| 0065-03 | 3.9 | 69:31 | 5 | Ethyl Acetate | TEC | 2 | NA | 0 | 0.42 | 1.46 |
| 0065-09 | 3.9 | 69:31 | 2 | Ethyl Acetate | NA | 0 | NA | 0 | 0.39 | 1.25 |
| 0065-10 | 1.9 | 69:31 | 2 | Ethyl Acetate | NA | 0 | NA | 0 | 0.35 | 1.18 |
| 0065-15 | 4.2 | 69:31 | 0.5 | Ethyl Acetate | NA | 0 | NA | 0 | 0.43 | 1.37 |
| 0065-16 | 4.1 | 69:31 | 0.5 | Methylene Chloride | NA | 0 | NA | 0 | 0.35 | 1.20 |
| 0065-17 | 4.1 | 69:31 | 0.5 | Ethyl Acetate | NA | 0 | PEG 1500 | 2 | 0.42 | 1.38 |
| 0065-18 | 4.2 | 69:31 | 0.5 | Methylene Chloride | NA | 0 | PEG 1500 | 2 | 0.38 | 1.23 |
| 0065-37 | 4 | 69:31 | 5.0 | Methylene Chloride | NA | 0 | NA | 0 | 0.34 | 1.19 |
| 0065-38 | 3.9 | 69:31 | 2.0 | Methylene Chloride | NA | 0 | NA | 0 | 0.30 | 1.02 |
| 0065-39 | 4.1 | 69:31 | 0.5 | Methylene Chloride | NA | 0 | NA | 0 | 0.32 | 1.09 |
| 0065-40 | 4 | 69:31 | 0.25 | Methylene Chloride | NA | 0 | PEG 1500 | 2 | 0.39 | 1.22 |

Example 3: Fabrication of Fiber Containing 2 wt % of Fluticasone Proprionate

A fiber formulation can be made with fluticasone proprionate with poly(DL-lactide) or poly(lactide-co-glycolide). The poly(lactide) or poly(lactide-co-glycolide) can be capped or have acid end groups. The desired fluticasone proprionate content in the fiber can range from 0.1 wt % to 20 wt %. To prepare a long-acting formulation of fluticasone proprionate, particles of fluticasone proprionate and poly (DL-lactide-co-glycolide) or poly(lactide-co-glycolide) can be dry blended in a variety of ways including the use of a mortar/pestle or by mixing preformed polymer and peptide particles in a V-blender to form a blended powder. Next this blend or admixture can be added to a twin-screw extruder having a machined die with a 2-mm diameter. The temperature of the extruder should be about 120° C. As the fiber is extruded from the extruder, it will be collected on a conveyor belt.

Example 4: Fabrication of Paranasal Sinus Device with Ribbon Fiber Containing 5 wt % Mometasone Furoate Ribbon fiber as prepared by Example 1, was fabricated into a paranasal sinus device in the following manner. Four strands of ribbon fiber were cut to approximately 35 mm and then looped to form whisk-like structures as previously described.

Example 5: Quantifying Mometasone Furoate Levels in the Sinus Tissue of Rabbits During Treatment with a Mometasone Furoate Loaded Paranasal Sinus Device Paranasal sinus devices prepared as described in Example 4 were sterilized with 2.5 Mrad of gamma radiation and placed in the maxillary sinuses (right and left sides) of 5-kg rabbits through dorsal nasal maxillary sinusotomies. Three formulations were tested. These were as follows:

PLG 69:31 with 5% mometasone and 0% triethylcitrate (TEC)
PLG 69:31 with 5% mometasone and 2% TEC
PLG 69:31 with 10% mometasone and 2% TEC The same formulation was used for both right and left sinuses of a given rabbit. Fifteen rabbits were implanted. Five rabbits were implanted with each device formulation. The devices were explanted at approximately weekly intervals post implantation over a 5-week period. The mucosa of both right and left maxillary sinuses was removed completely at the time of explanation. The tissue was rapidly frozen and the amount of mometasone in the tissue was quantitated by liquid chromatography/mass spectroscopy (LC/MS). The amount of mometasone maintained in the tissue over a 35-day period is reported in the table below, and is equivalent to $10^{-5}$ M to $10^{-7}$ M concentration at the desired site of action, at all time points demonstrating a sustained release and bioavailability of drug at levels of tissue concentration which are known to have therapeutic efficacy (see below).

| | | Mometasone Levels Measured in Excised Sinus Mucosa (micrograms Mometasone per gram tissue) | | | | |
|---|---|---|---|---|---|---|
| | | 4 day pooled | 14 day | 25 day | 30 day | 35 day |
| 10% Mometasone 2% TEC | R | 0.915 | 1.41 | 183 | 139 | 97.6 |
| | L | 0.823 | 5.95 | 7.57 | 152 | 335 |
| 5% Mometasone 2% TEC | R | 1.17 | 1.01 | 1.44 | 0.76 | 81.7 |
| | L | (st dev = | No peak | 44.3 | 86.4 | 153 |
| 5% Mometasone 0% TEC | R | 0.18) | 246 | 1.28 | 2.11 | 178 |
| | L | | 2.57 | | 0.54 | 158 |

Example 6: In Vitro Release of Mometasone Furoate from Candidate Compositions

Figure 25:
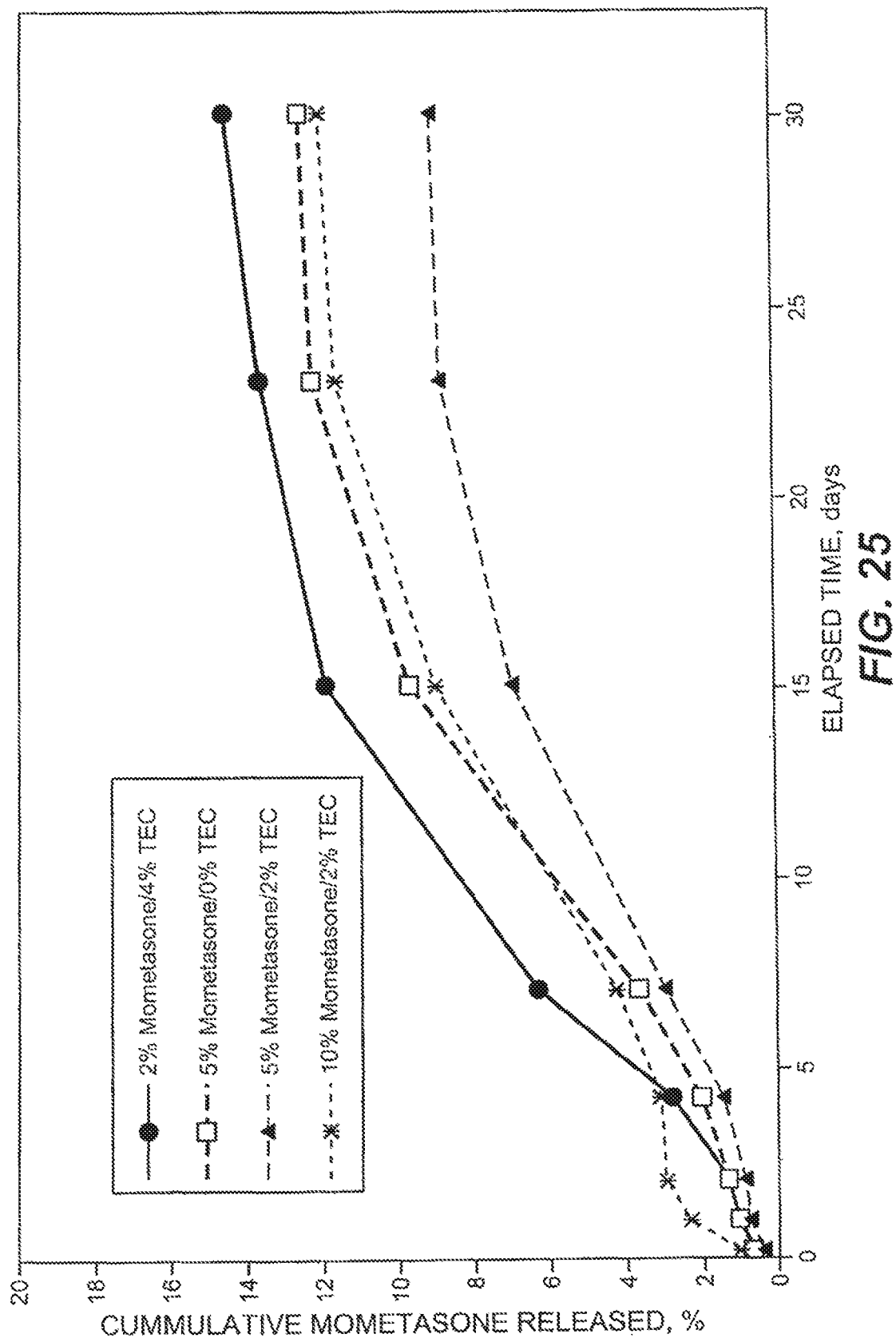
FIG. 25 is a graph showing cumulative in vitro release of mometasone furoate from various paranasal sinus devices over a 30-day time period.

The in vitro release of mometasone furoate from candidate formulations was determined, and is shown in FIG. 25. To carry out this in vitro release study, each device was placed at 37° C. in 1.0 wt % sodium dodectyl sulfate (SDS) in nanopure water, the receiving fluid. At each time point, the receiving fluid was removed completely and fresh receiving fluid was added. The amount of mometasone released into the receiving at each time point was quantified by HPLC.

In a first in vitro cumulative release study, as shown in FIG. 25, cumulative release of mometasone furoate from a 2% mometasone/4% TEC fiber was about 6% at day 7, about 11% at day 14, about 14% at day 21, and about 15% at day 28. For the 5% mometasone/0% TEC fiber, cumulative mometasone release was about 4% at day 7, about 10% at day 14, about 12% at day 21, and about 12 at day 28. The 5% mometasone/2% TEC fiber cumulative mometasone release was about 3% at day 7, about 7% at day 14, about 9% at day 21, and about 9% at day 28. For the 10% mometasone/2% TEC fiber, cumulative mometasone release measured to be about 4% at day 7, 9% at day 14, 12% at day 21, and 12% at day 28. Additional drug release due to in vivo polymer biodegradation and clearance was demonstrated and directly observed as described above in the tissue concentration data.

Published in vitro cellular models using cultured human airway epithelial cells indicate drug concentration dose response curves for the most potent glucocorticoids, mometasone furoate and fluticasone propionate, beginning as low as $10^{-12}$M (picomolar) and $EC_{50}$ levels of transcriptional response at $10^{-10}$ M (100 picomolar; maximal transcriptional response was seen in most cases by $10^{-9}$ M (nanomolar) drug concentrations). These in vitro models have been accepted as equivalent to and highly correlated with in vivo models of efficacy (Romestan C. et al Fluticasone Propionate and Mometasone Furoate Have Equivalent Transcriptional Potencies, Clin Exp Allergy 2003; 33: 895-901).

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed as new and desired to be protected by Letters Patent of the United States is:

1. A paranasal sinus device comprising:
   a bioabsorbable expandable cavity member having a proximal end and a distal end, and sized and shaped to fit within a paranasal sinus cavity, wherein the expandable cavity member comprises a pronged structure comprising three or more filaments that are pliable and partially curved, and which flex radially outwardly to contact sinus mucosa, each of the three or more filaments having a length between about 2 cm and about 5 cm, a proximal end, and a distal end, wherein the distal ends are free distal ends, and wherein the free distal ends define the distal end of the cavity member, and further wherein the expandable cavity member is self-expanding.

2. The paranasal sinus device of claim 1, wherein the expandable cavity member is configured to biodegrade.

3. The paranasal sinus device of claim 2, wherein the expandable cavity member comprises one or more biodegradable polymers.

4. The paranasal sinus device of claim 1, wherein the expandable cavity member is configured to release one or more active agents.

5. The paranasal sinus device of claim 4, wherein the one or more active agents comprises mometasone furoate.

6. The paranasal sinus device of claim 1, wherein the expandable cavity member comprises one or more radiopaque markers.

7. The paranasal sinus device of claim 1, further comprising one or more anchoring elements on each filament, wherein the anchoring elements are configured to anchor the expandable cavity member within the paranasal sinus cavity.

8. The paranasal sinus device of claim 1, wherein each filament is formed from an extruded polymer.

9. A paranasal sinus device comprising:
   a bioabsorbable expandable cavity member having a proximal end and a distal end, and sized and shaped to fit within a paranasal sinus cavity, wherein the expandable cavity member comprises a pronged structure comprising a plurality of filaments that are pliable and partially curved, and which flex radially outwardly to contact sinus mucosa, each filament of the plurality of filaments having a length between about 2 cm and about 5 cm, a proximal end, and a free distal tip, wherein the free distal tips define the distal end of the cavity member, and
   further wherein the expandable cavity member is self-expanding.

10. The paranasal sinus device of claim 9, wherein the expandable cavity member comprises one or more biodegradable polymers.

11. The paranasal sinus device of claim 9, wherein the expandable cavity member is configured to release one or more active agents.

12. The paranasal sinus device of claim 11, wherein the one or more active agents comprises mometasone furoate.

* * * * *